US009833381B2

(12) United States Patent
Caetano

(10) Patent No.: US 9,833,381 B2
(45) Date of Patent: Dec. 5, 2017

(54) SPIKE-TYPE CONNECTOR FOR A MEDICAMENT RECONSTITUTION BAG, AND SAFETY DEVICE FOR A BOTTLE CONTAINING A MEDICAMENT TO BE RECONSTITUTED

(76) Inventor: Norival Caetano, São Paulo (BR)

( * ) Notice: Subject to any disclaimer, the term of this patent is extended or adjusted under 35 U.S.C. 154(b) by 925 days.

(21) Appl. No.: 13/876,681

(22) PCT Filed: Sep. 2, 2011

(86) PCT No.: PCT/BR2011/000314
§ 371 (c)(1),
(2), (4) Date: Jul. 11, 2013

(87) PCT Pub. No.: WO2012/040799
PCT Pub. Date: Apr. 5, 2012

(65) Prior Publication Data

US 2013/0306509 A1 Nov. 21, 2013

(30) Foreign Application Priority Data

Sep. 29, 2010 (BR) ...................................... 1003460

(51) Int. Cl.
*A61M 5/32* (2006.01)
*A61J 1/20* (2006.01)
(Continued)

(52) U.S. Cl.
CPC ................... *A61J 1/20* (2013.01); *A61J 1/10* (2013.01); *A61J 1/1412* (2013.01); *A61J 1/1481* (2015.05);
(Continued)

(58) Field of Classification Search
CPC .......... A61J 1/1481; A61J 1/20; A61J 1/2062; A61J 1/2065; A61J 1/2055; A61J 1/2096;
(Continued)

(56) References Cited

U.S. PATENT DOCUMENTS 4,632,267 A * 12/1986 Fowles ..................... A61J 1/10
215/253
7,358,505 B2 4/2008 Woodworth et al.
(Continued)

FOREIGN PATENT DOCUMENTS

| | | | |
|---|---|---|---|
| BR | 0311342 | A | 3/2005 |
| EP | 0766955 | A1 | 4/1997 |
| EP | 1 605 891 | | 12/2005 |
| WO | 99/59522 | A1 | 11/1999 |
| WO | 03/099191 | A1 | 12/2003 |
| WO | 2004/084793 | A1 | 10/2004 |

OTHER PUBLICATIONS

International Search Report dated Jan. 19, 2012; PCT/BR2011/000314.

*Primary Examiner* — Tatyana Zalukaeva
*Assistant Examiner* — Ariana Zimbouski
(74) *Attorney, Agent, or Firm* — Ladas & Parry LLP

(57) ABSTRACT

A bag having two accesses, an inlet and an outlet, both containing closing devices for releasing or stopping the flow of a liquid that flows into or out of the bag. The inlet has a filtering element for retaining particles possibly produced by the coring phenomenon which can occur when the spike of the inlet ruptures the plug of the bottle. Also provided is a safety device used for permanently attaching the bottle to the inlet.

3 Claims, 28 Drawing Sheets

(51) Int. Cl.
*A61J 1/10* (2006.01)
*A61J 1/14* (2006.01)

(52) U.S. Cl.
CPC ........... *A61J 1/2089* (2013.01); *A61J 1/2096* (2013.01); *A61J 1/1443* (2013.01); *A61J 1/201* (2015.05); *A61J 1/2031* (2015.05); *A61J 1/2041* (2015.05); *A61J 1/2051* (2015.05); *A61J 1/2055* (2015.05); *A61J 1/2086* (2015.05)

(58) Field of Classification Search
CPC .......... A61J 1/2089; A61J 1/1475; A61J 1/10; A61J 1/22; A61J 1/2006; A61J 1/2013; A61J 1/201; A61J 1/2086; A61J 1/1412; A61M 5/5086; A61M 5/344
See application file for complete search history.

(56) References Cited

U.S. PATENT DOCUMENTS

| | | | | |
|---|---|---|---|---|
| 7,425,209 | B2 | 9/2008 | Fowles et al. | |
| 2004/0199139 | A1* | 10/2004 | Fowles ................. | A61J 1/1406 604/414 |
| 2005/0215943 | A1* | 9/2005 | Brandenburger ..... | A61J 1/1475 604/30 |
| 2008/0300570 | A1 | 12/2008 | Fowles et al. | |
| 2009/0216212 | A1 | 8/2009 | Fangrow, Jr. | |
| 2009/0270832 | A1* | 10/2009 | Vancaillie ............. | A61J 1/1475 604/408 |
| 2013/0053814 | A1* | 2/2013 | Mueller-Beckhaus ............. | A61J 1/2096 604/414 |

* cited by examiner

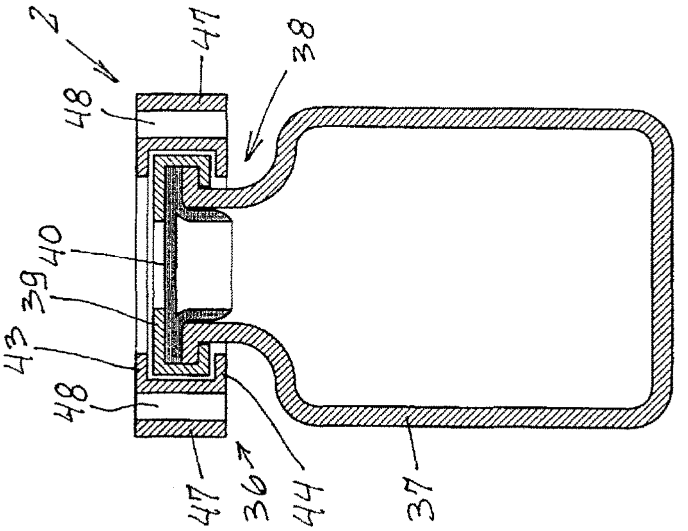
FIG. 8 (A-A)
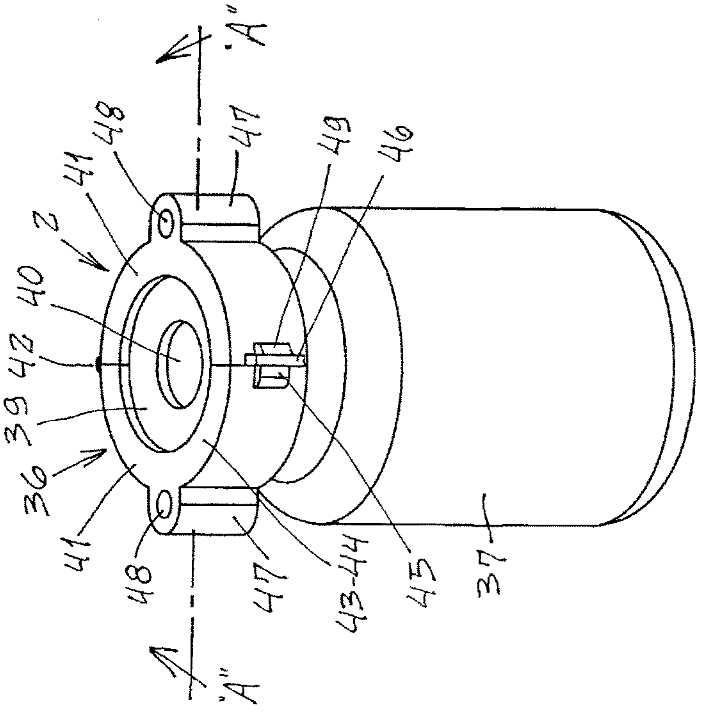
FIG. 7

SPIKE-TYPE CONNECTOR FOR A MEDICAMENT RECONSTITUTION BAG, AND SAFETY DEVICE FOR A BOTTLE CONTAINING A MEDICAMENT TO BE RECONSTITUTED

The present report is related to a patent of Invention Privilege which proposes a bag for conditioning, reconstitution and/or dilution of injectable products, which may be used for medicament administration preferably of human use. The present patent of Invention Privilege is further related to a safety device applicable to a bottle containing a medicament to be reconstituted and/or diluted in said bag here proposed. The safety device here proposed prevents one bottle containing a medicament to be reconstituted and/or diluted, and which has been connected to the model of bag in question, from being later separated from the bag. While remaining attached to the bag, the bottle identifies the product which was or will be transferred to the bag, identifying product name, manufacturing laboratory, concentration, route of administration, manufacturing date, validity term, number of batch and prior storage conditions required.

As known by general medical area professionals and more specifically in relation to pharmaceutical area professionals, the manufacture of parenteral administration products (injectable) poses a fascinating challenge to the pharmaceutical industry in terms of technical design, validation processes, and personnel training and preparation of challenge testing to aseptic integrity of the final product and the system producing it.

As it is known, the pharmaceutical industry has mastered a sophisticated production technique, providing the market with injectable products which are basically of two kinds: a) products manufactured by aseptic processes; and b) products which after a clean procedure chain go through a final sterilization.

The pharmaceutical products are marketed in their final utilization form (liquid products) or in a prior phase, as powders to be reconstituted (injection powder).

Keeping in mind that only products in their liquid form may be injected, the concept to be established is related to such transfer of responsibility which is to provide the consumer market with powder products for injectable preparation. A sterile powder or lyophilized powder product must be understood and “non final” product, or “not finished”, which will require extra work so as to become injectable. These products exist because that was the way found by the pharmaceutical industry to ensure better stability and enable thus longer storage periods of time, which would not be possible if certain products were delivered already in the liquid form in the manufacturing units.

The pharmaceutical industry, in case of a powder-like product for injectable preparation, thus transfers to health professionals one phase of the “manufacturing process” of such product, as already mentioned the powder reconstitution with a proper diluent. In order to settle such transfer concept and understand how this phase is fundamentally important, it is necessary to remind that the product reconstituted starts presenting a stability other than that of powder, depending on the diluent, volume used and exposure conditions such as temperature and light.

It must be remembered here that in the powder manufacturing process (and also obviously in the injectable liquid product manufacturing), the pharmaceutical industry had to struggle during the whole industrial phase, among other factors, with the powder sterility and with a strict limit of particulate material, which consists of foreign microscopic particles eventually present in the product.

It must be remembered further that there are pharmacopoeic limits for particles with 10 micron of diameter and particles with 25 micron of diameter, stressing out that particles visible to the naked eye, here deemed particles bigger than 50 micron of diameter, are strictly forbidden and require segregation and product destruction.

Based on the presupposition that there are limitations for the number of microscopic particles in a product, in addition to the prohibition of the presence of visible particles, it is easy to understand that this is equally worth for the powder reconstitution phase (that product preparation phase transferred to the health professional).

Inside such context how can it be understood then that we can allow that corks are punctured with plastic spikes or even with thick gauge metallic needles with elementary protection of a filter?

The particle detection testing in injectable products take into consideration pharmacopoeic limits for cork puncturing operations with metallic needles of 0.8 mm of external diameter (21 gauge) (chapter 381 of The United States Pharmacopeial Convention, 2010) and does not even far mention plastic spikes, which every day cause these corks coring (displacement of particles), besides the notorious fact that most hospitals prepare injectable products by puncturing corks with needles of gauge not referred to, the needles with 1.2 mm of external gauge are the most common used in such services.

Considering further that many products are prepared in unsuitable locations and also considering the precarious qualification of many hospital attendants, in addition to the particles present in the products (result of coring), many times the product aseptic conditions are compromised, without mentioning the common exchange of diluents forbidden or not recommended or in wrong volumes. It must be stressed out also that some products further produce air bubbles or gases during preparation and make even more difficult the visualization of particles inside it.

From the biologic point of view, the biggest fear placed by the presence of particles in an injectable product is the embolization possibility: occurrence where the particle injected through the blood current may obstruct one vessel and compromise important organs as lungs and brain.

There is also the possibility of cork particles forming granulomas (inflammatory nodular formations around particles). If the doctors are not aware of such possibilities, clinical manifestations resulting therefrom might not be diagnosed or be attributed to other factors.

Thus, the handling and administration of injectable products many times compromise the enormous effort previously made by the pharmaceutical industry in its obligation of providing sterile products and free of particles.

Developing techniques, materials and equipment which intend to ensure the handling, identification and aseptic administration of injectable products, particularly powder-like products for injection, must be a constant concern.

As regards the practice of injectable product administration, many products are conditioned originally in their liquid form in plastic bags (medicaments or diluents), while other products require the passage through one plastic bag during preparation and/or administration phase. Inside such bag, therefore, one originally-liquid product may be stored, a liquid product may be diluted or a powder-like product may be reconstituted and/or diluted.

One plastic bag must ensure the integrity, in terms of asepsis and by the absence of fragments (mainly cork particles) in its interior, must be further of easy handling, must allow fast visual identification of what will be injected and must also allow safe fractioning of the product when a lower dose is desired, for example, for children or patients bearing renal insufficiency.

Several bags existing in the market try to comply with such purposes, although none covers all such aspects. The bags pertaining to the art work with unsafe items, such as plastic spikes (needles) with filter incorporation (during cork perforation, the spikes drop particles inside the system), present rubber corks and silicon doors in addition to plastic seals which are broken in contact with the solution, and all such items generate particles. It is worth remembering that solutions containing particles must be promptly discarded for obvious safety reasons from the patient's point of view.

In face of the aspects above covered in relation to the art of bags normally used for conditioning, reconstitution and/or dilution of injectable products, the present patent of Invention Privilege was developed, which proposes a bag of the nature above defined into which several improvements were introduced so that such improvements jointly basically eliminate the troubles verified in the art related to such item.

The object addressed in this request of patent of Invention Privilege consists of a bag built in order to ensure an easy handling of injectable products, always keeping in mind that the aseptic technique rules of preparation and administration must be respected.

Objectively, the bag now discussed presents a series of innovative technical characteristics, which comprise, for example, the fact that the same if fitted with a spike (plastic needle) fitted with own protection filter. The filter, placed in the spike base and immediately before the "open-and-close" door, ensures the particle retention. Since such filter is placed before the "open-and-close" door, it will only be in touch with the bag solution upon its actual use. According to what was set forth in this patent of Invention Privilege, there is no contact between liquid and filter during bag storage, whereas such characteristic in particular allows that there is not any interference in relation to the validation of liquid contained in this bag.

The bag object of the patent of Invention Privilege differs from similar products belonging to the art by the fact that it owns a bottle locking system which makes accidental or intentional product exchanges difficult and allows the bottle facilitated identification which remains affixed. This, in case of powder reconstitution for injection, complies with the concept that such operation is part of "injectable product manufacturing process", and the reconstituted product will remain properly identified. The bottle attached to the spike, by means of its label, informs product name, manufacturing laboratory, route of administration, manufacturing date, validity term, manufacturing batch number and allows also to identify the product amount placed inside the bag, in addition to prior storage conditions required.

Another innovative characteristic of the bag object of this patent of Invention Privilege is the fact that the same does not present rubber or silicone doors (which generate particles) and it also presents own filter which avoids cork fragments and other particles which would pass from the bottle to the bag when the spike punctures the bottle cork.

Another innovative aspect of the bag design here discussed is the fact that the same presents in its bottle-attaching door one open-and-close system initially sealed (Seal) to ensure the system integrity and that, when opened, it allows the passage of the liquid for product reconstitution and/or dilution. The system is closed, after product preparation, in order to ensure the non-return of product reconstituted and/or diluted to the bottle preventing thus one loss of product during the infusion process.

The bag here discussed presents also the innovative characteristic of displaying one output door with open-and-close system to ensure the easy and safe attachment of the infusion equipment, which must be equipment with luer lock attachment, or of a syringe equally with luer lock tip to withdraw the fractioned dose whenever required. It is worth stressing out that this bag will require us to replace the plastic spike terminations of the infusion equipment with luer lock termination. This exchange with lock luer terminations in the infusion equipment will avoid usual accidents to which nurses are subject to while handling the spikes of traditional equipment, in addition to the additional advantage of eliminating another factor of coring (loosening up of particles) when the infusion equipment spikes puncture the rubber doors or silicon doors of traditional bags. The luer lock terminations are not pointed and, therefore, are not piercing.

This output door may also be calibrated to allow, during the infusion process, one planned dripping (remaining fixed at one phase, it allows certain maximum of flow, avoiding thus the administration of toxic doses or hurtful doses due to speed of administration).

At last, another innovative characteristic of the bag design here discussed is the fact that the same may also eliminate the attachment door to the bottle (the door usually fitted with spike), it remaining only with one open-and-close door, for example, to condition diluents or other liquid products. The open-and-close mechanism proposed by the present patent facilitates the attachment to infusion lines, which must use luer lock attachments, as we already described, and allows the safe fractioning of doses as we already emphasized.

Another purpose of this patent of Invention Privilege is to provide one safety device which operates jointly with the bag here discussed, said safety device is intended to be assembled next to a bottle bottleneck of medicament, it being sealed in relation to the same and bearing further the capacity to establish one form of inviolable adhesion with the bag here described.

The safety device now presented has as function to ensure that the bottle for medicament fitted with the same, after being connected to the input door of the bag now discussed, cannot be later removed, ensuring the fast identification of the which was or will be reconstituted and/or diluted.

The bag and the safety device here discussed and which are object of this patent of Invention Privilege may be understood as regards to all their innovative aspects from the detailed description which will be done based on the corresponding drawings below, in which:

FIG. 7 shows the safety device duly assembled next to the bottleneck of one generic model of a bottle containing a medicament, said device being in its condition of total locking in relation to the bottle, which prevents separation of both;

FIG. 8 shows a section taken of FIG. 7, such as that indicated by the line of section "A"-"A", section which clearly and objectively shows how the safety device assembly occurs in relation to the bottleneck of one generic model of a bottle containing a medicament of the kind that may be attached to the bag here discussed;

Figure 9:
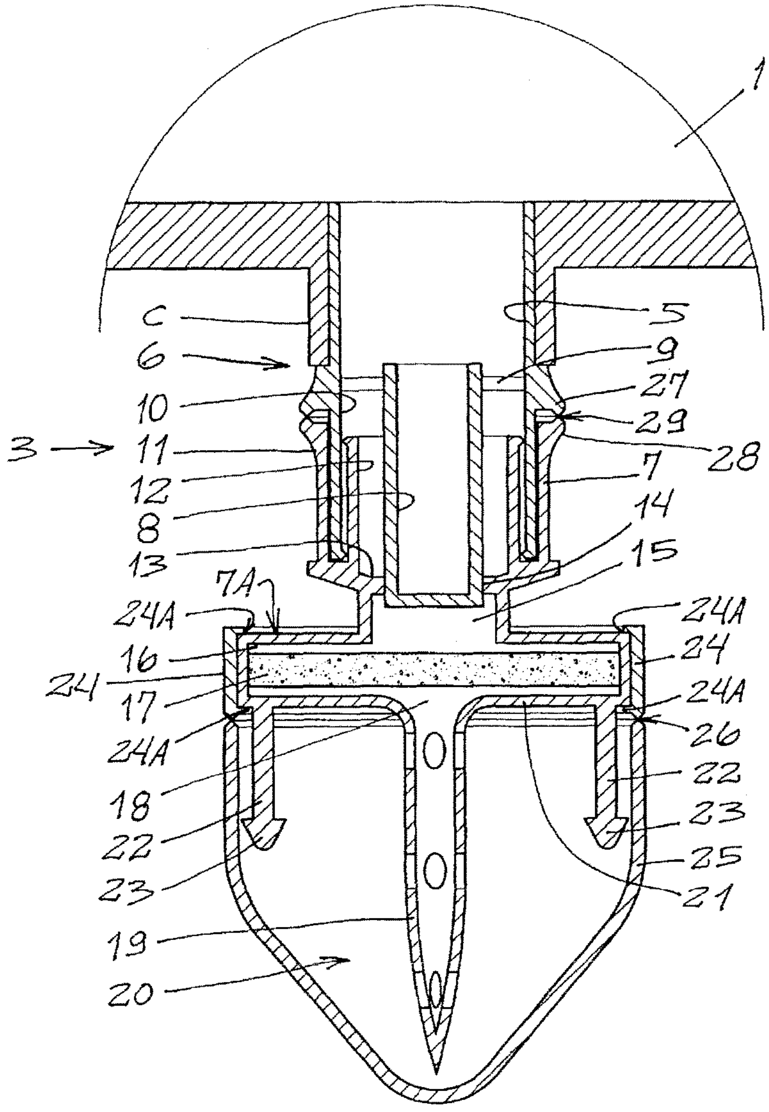
FIG. 9 shows one view in full section of the input door which is integral part of the bag model here presented, said input door is represented in its closed condition and with its sealing means still intact.
Figure 10:
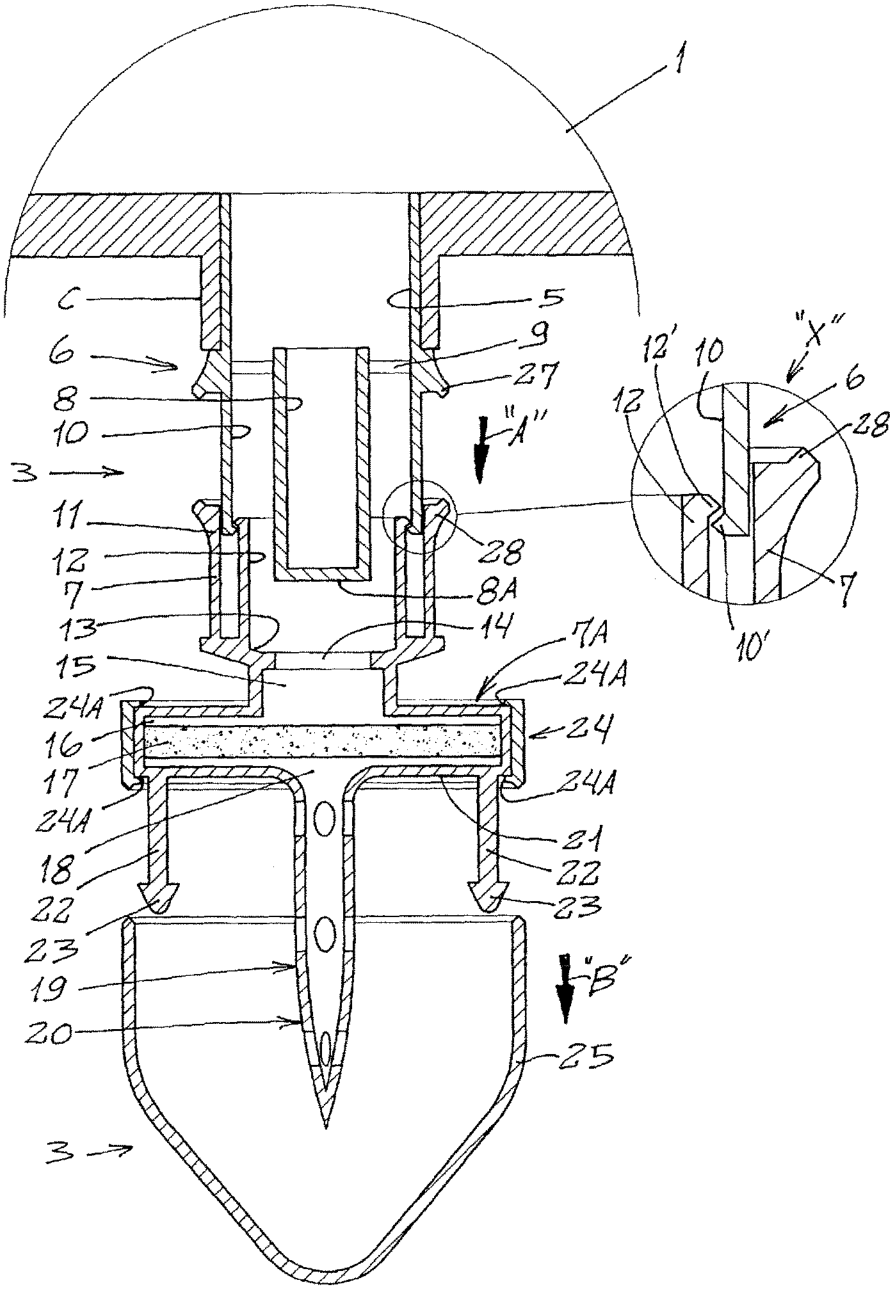
Figure 11:
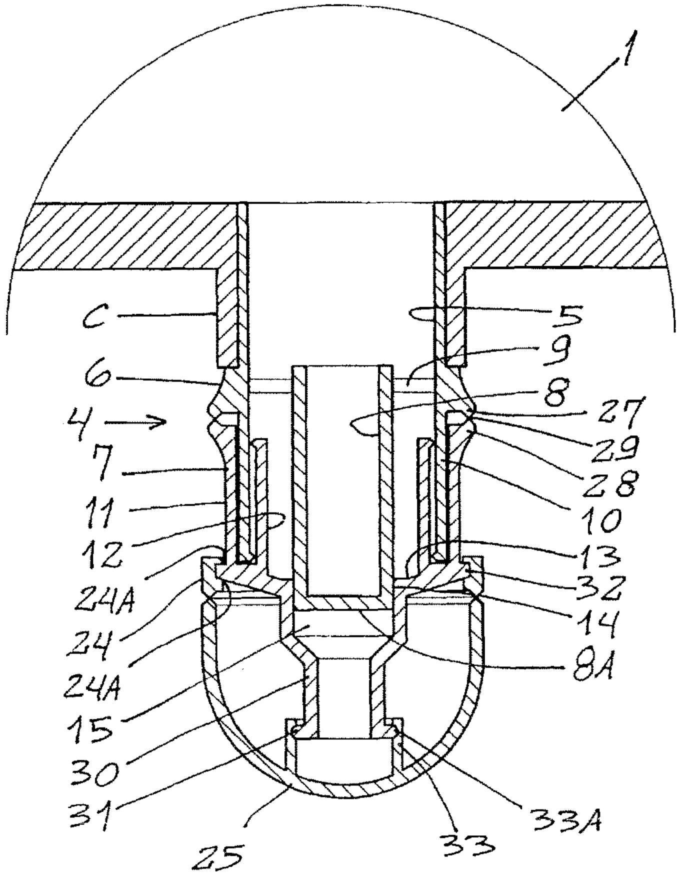
Figure 12:
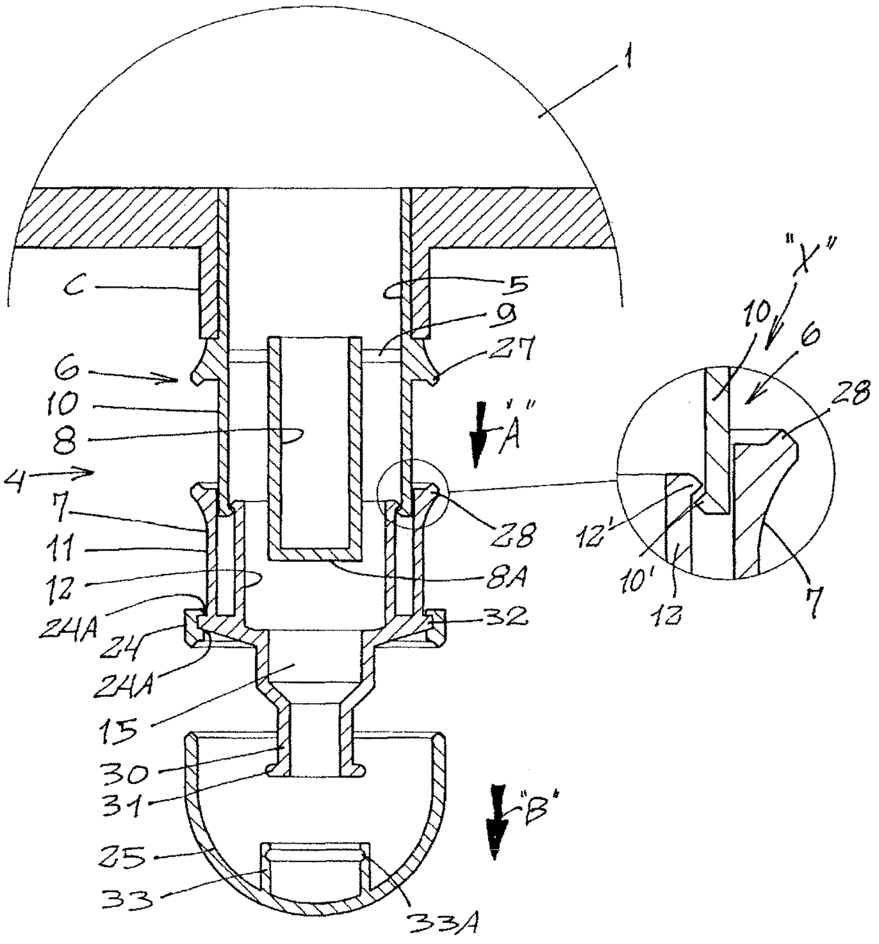
Figure 13:
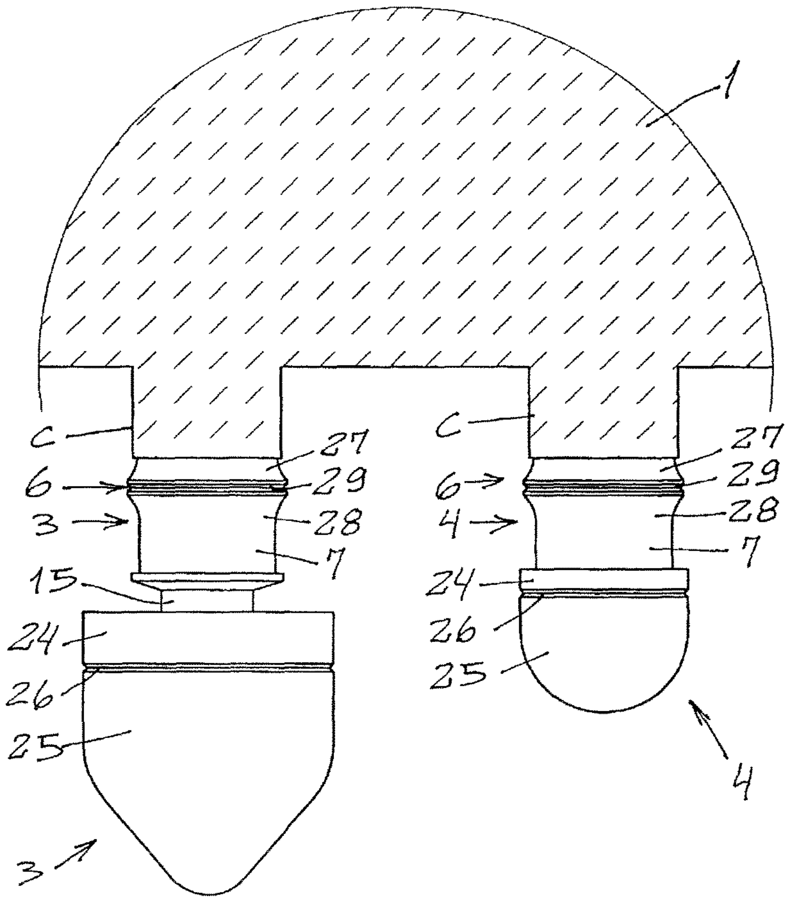
Figure 14:
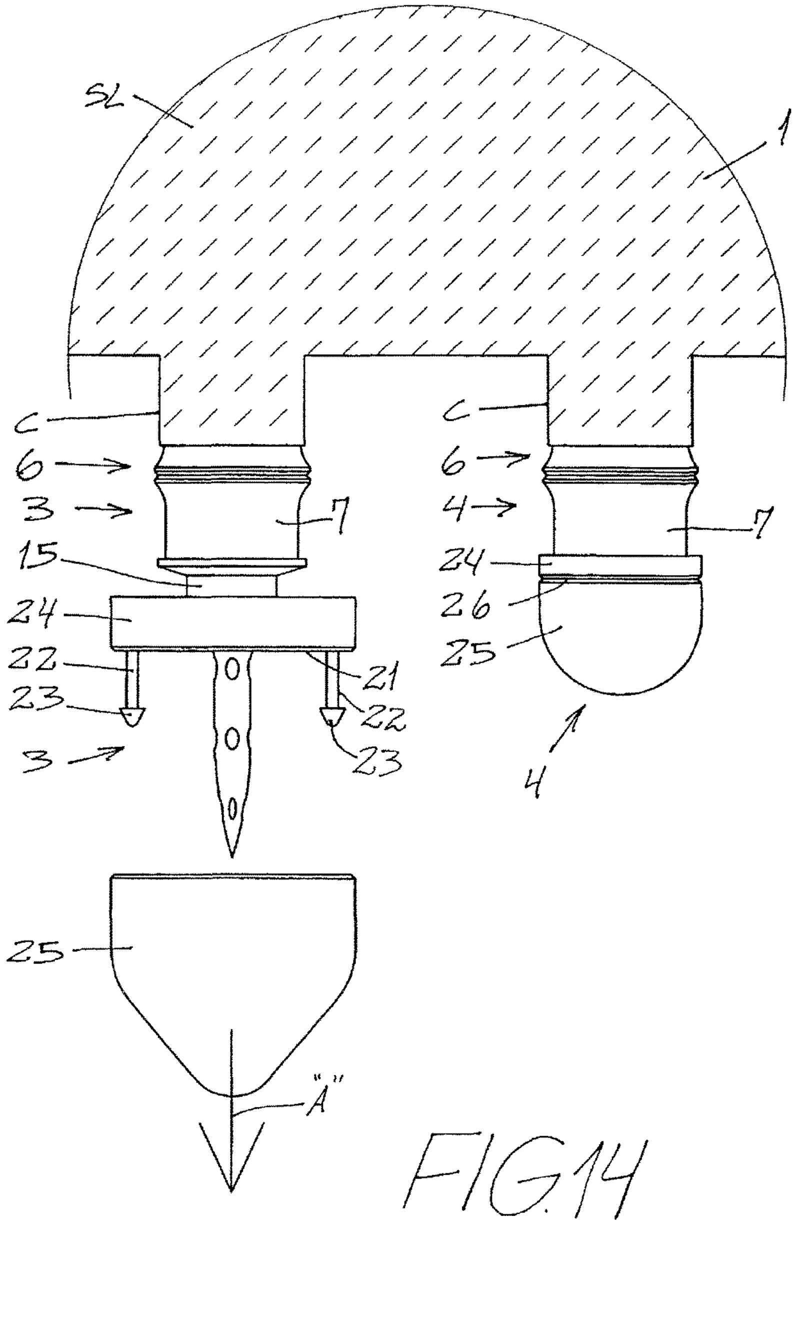
Figure 15:
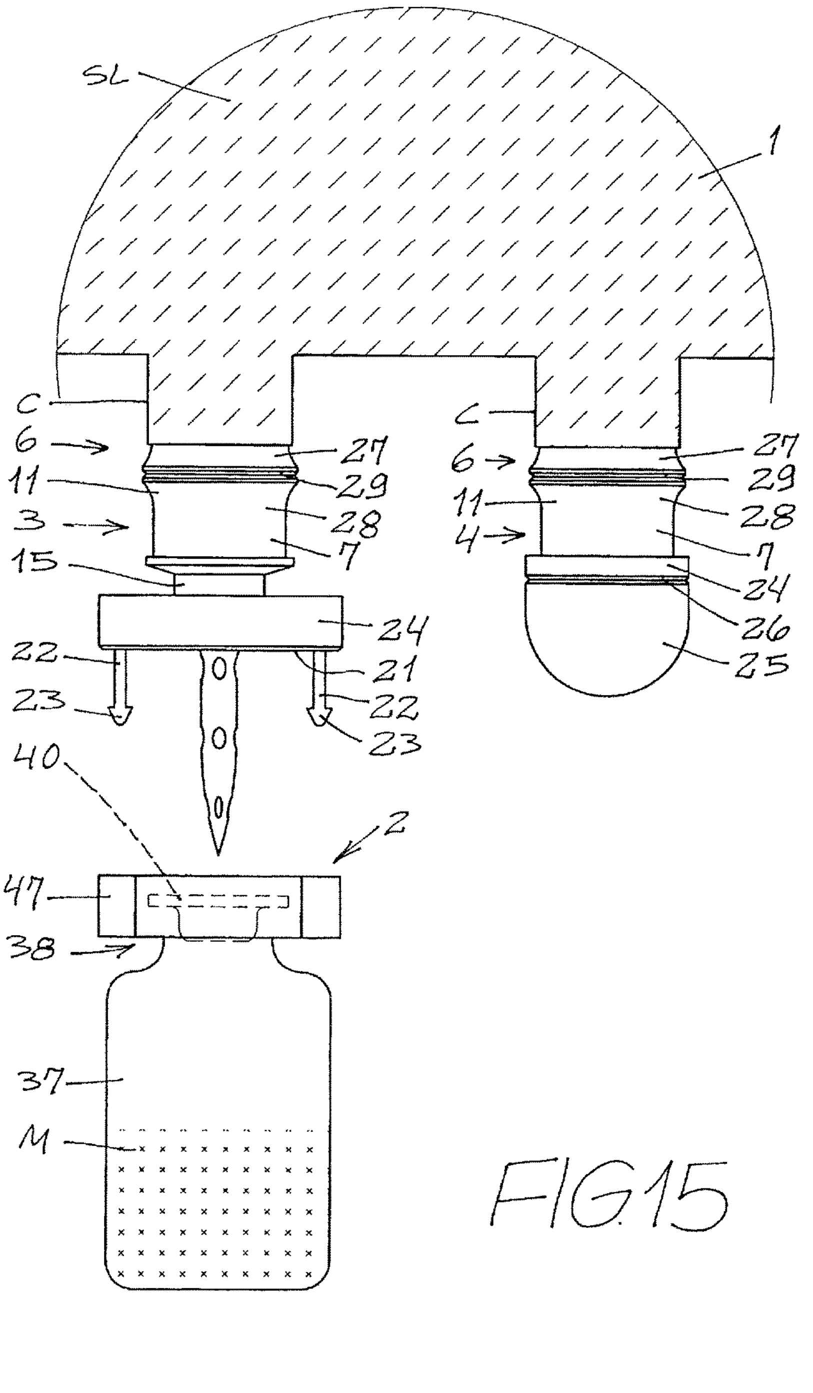
Figure 16:
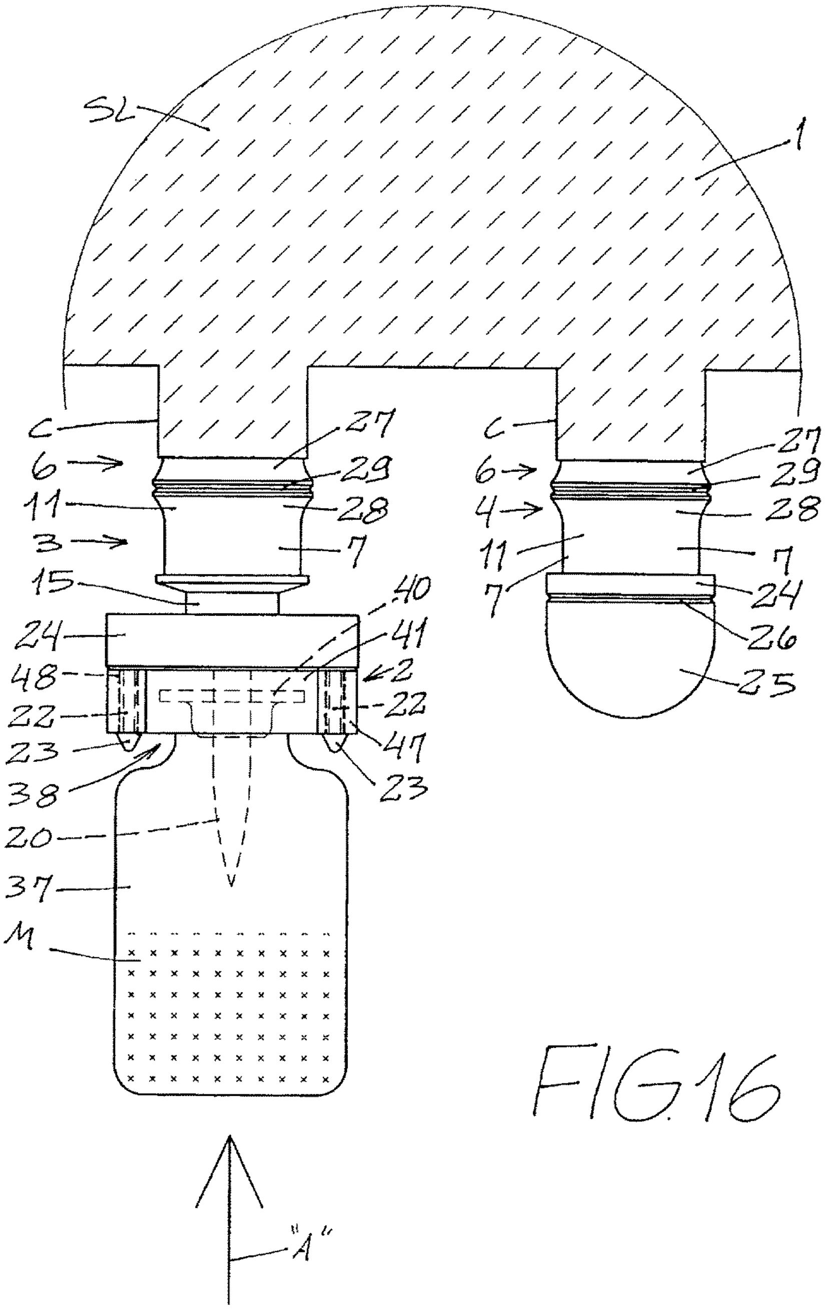
Figure 16A:
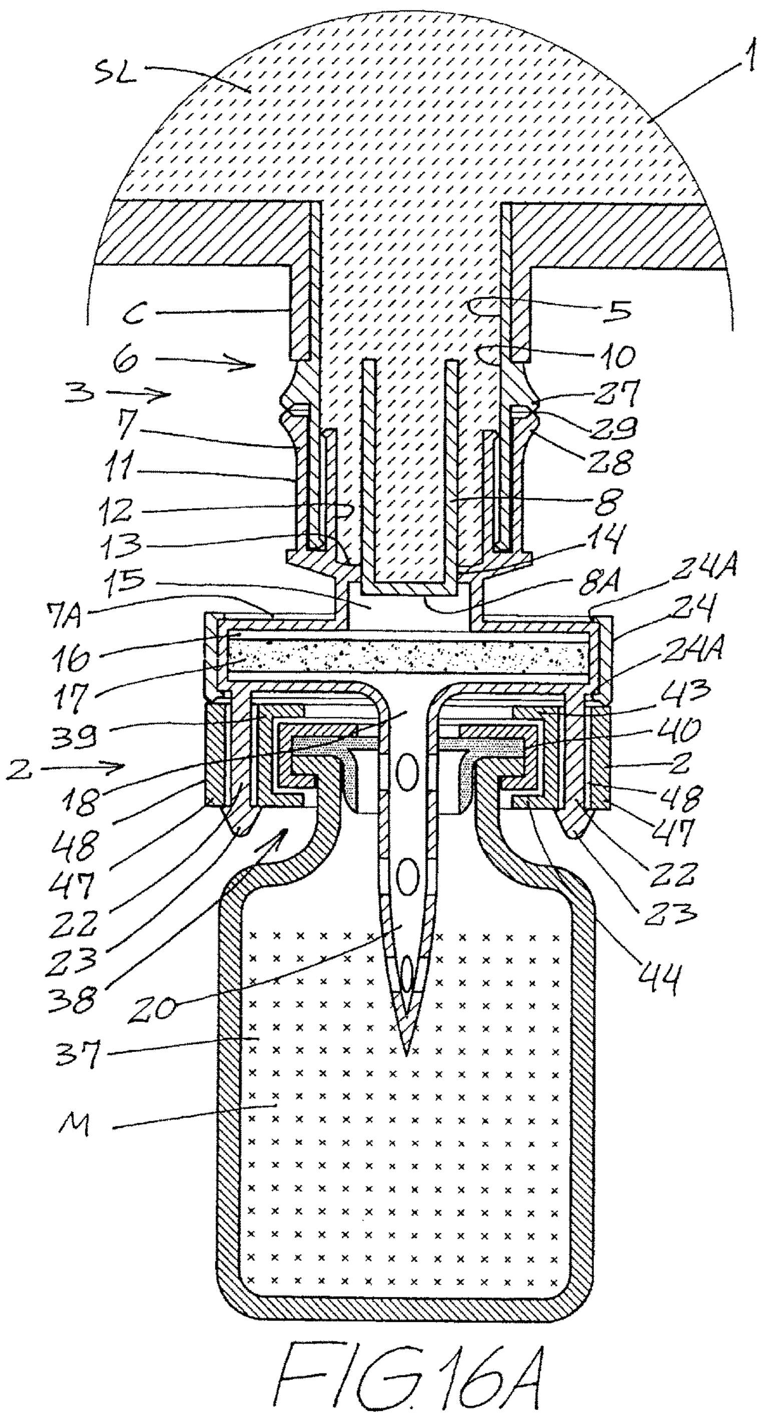
Figure 17:
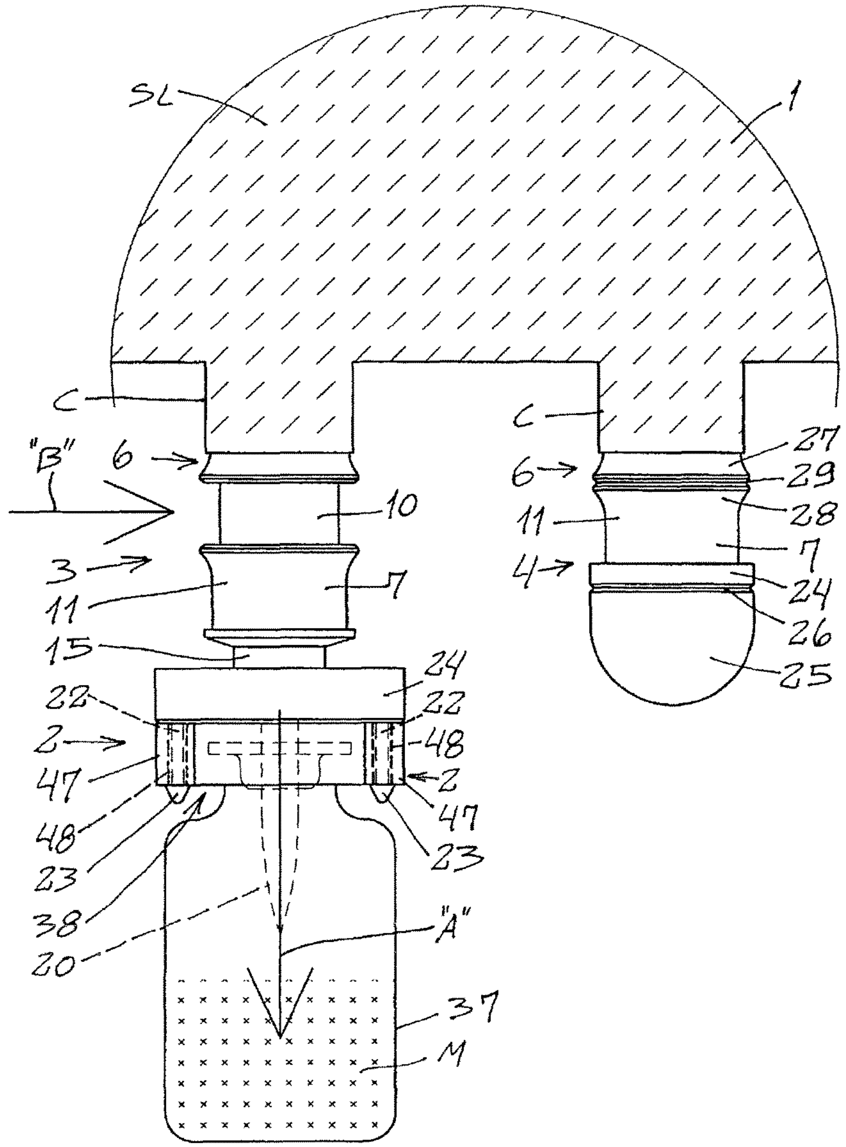
Figure 18:
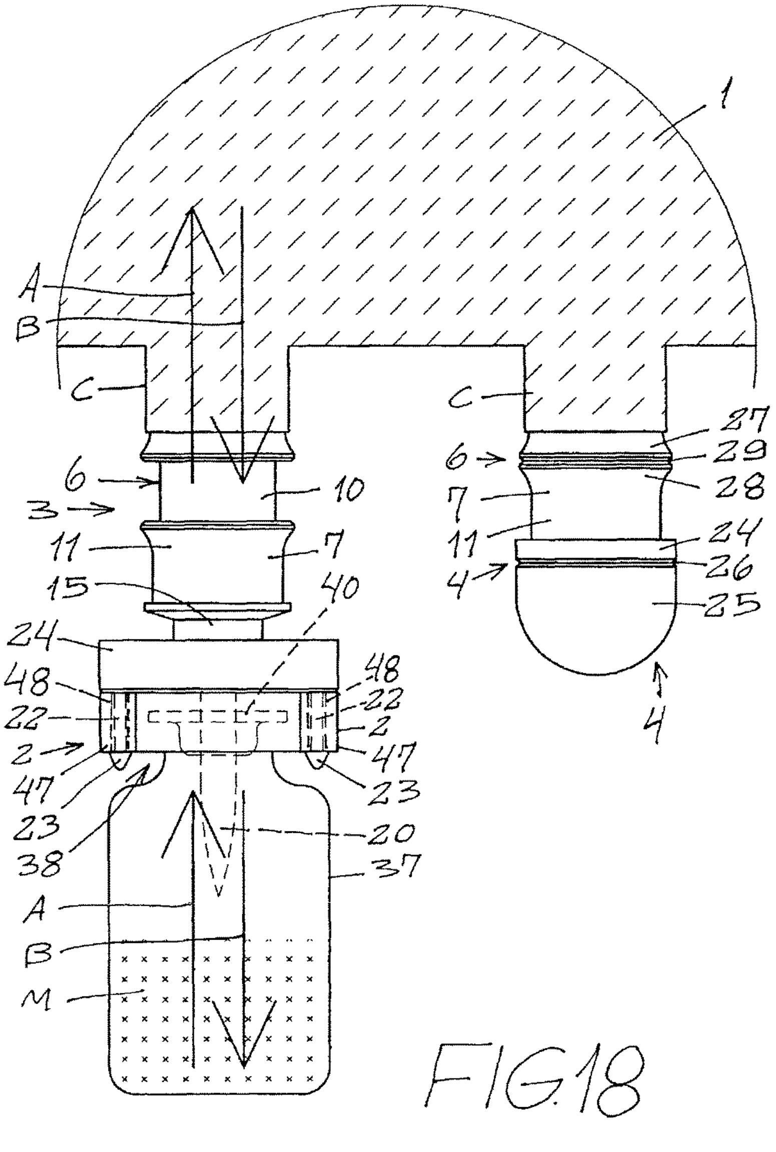
Figure 19:
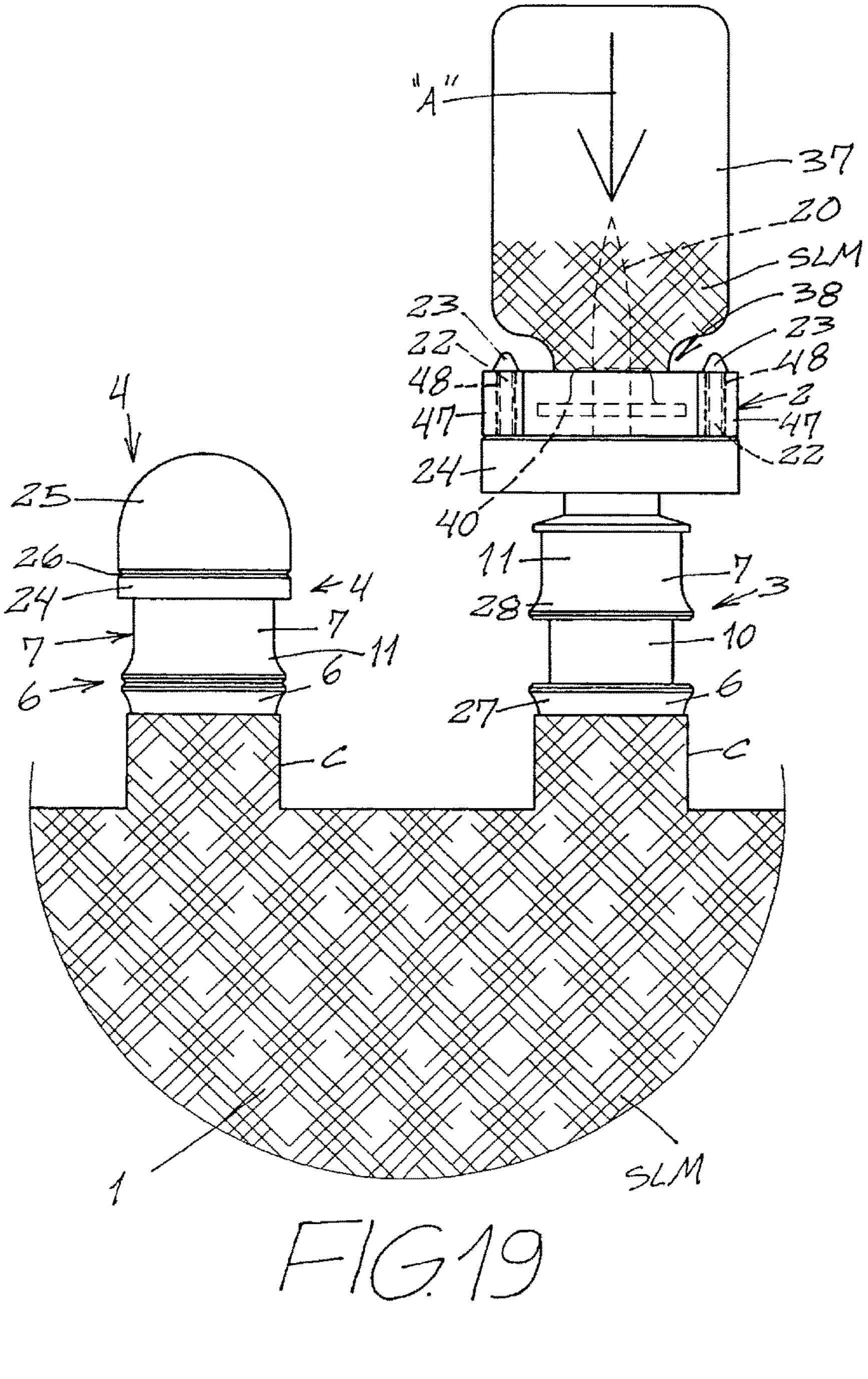
Figure 19A:
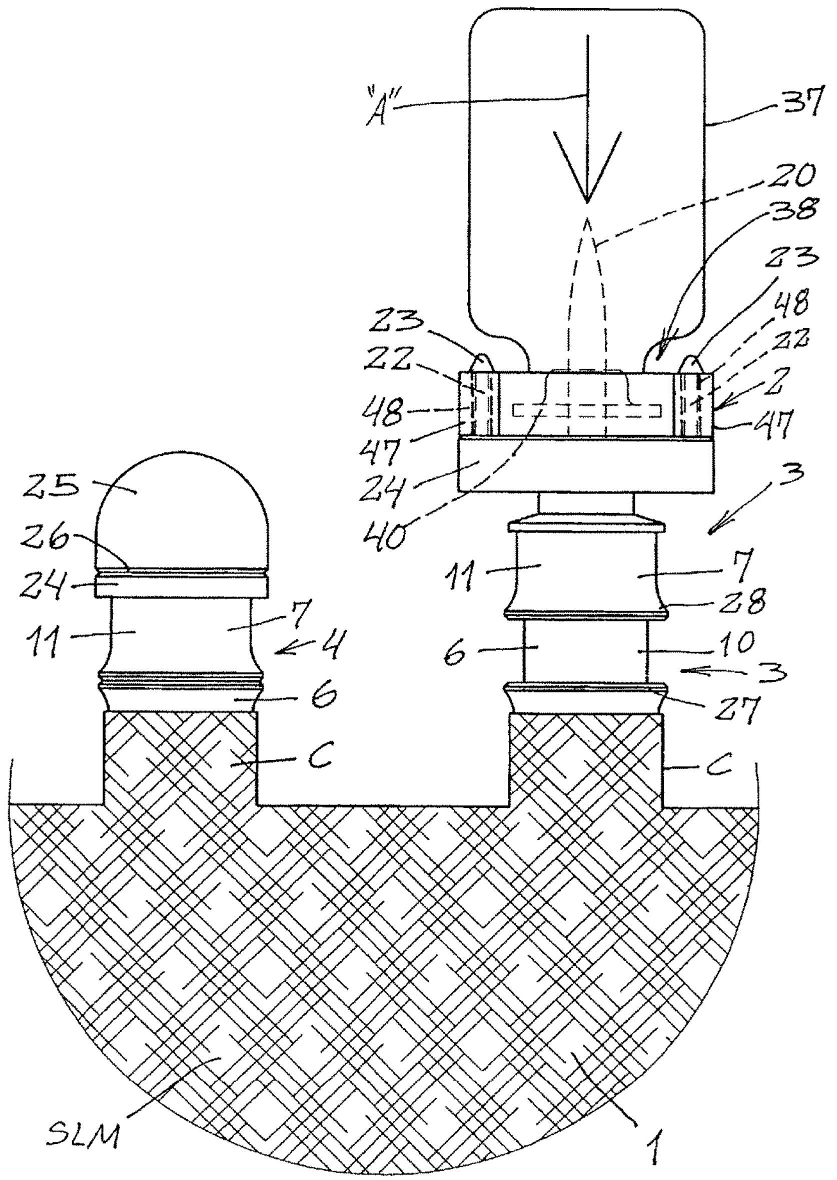
Figure 20:
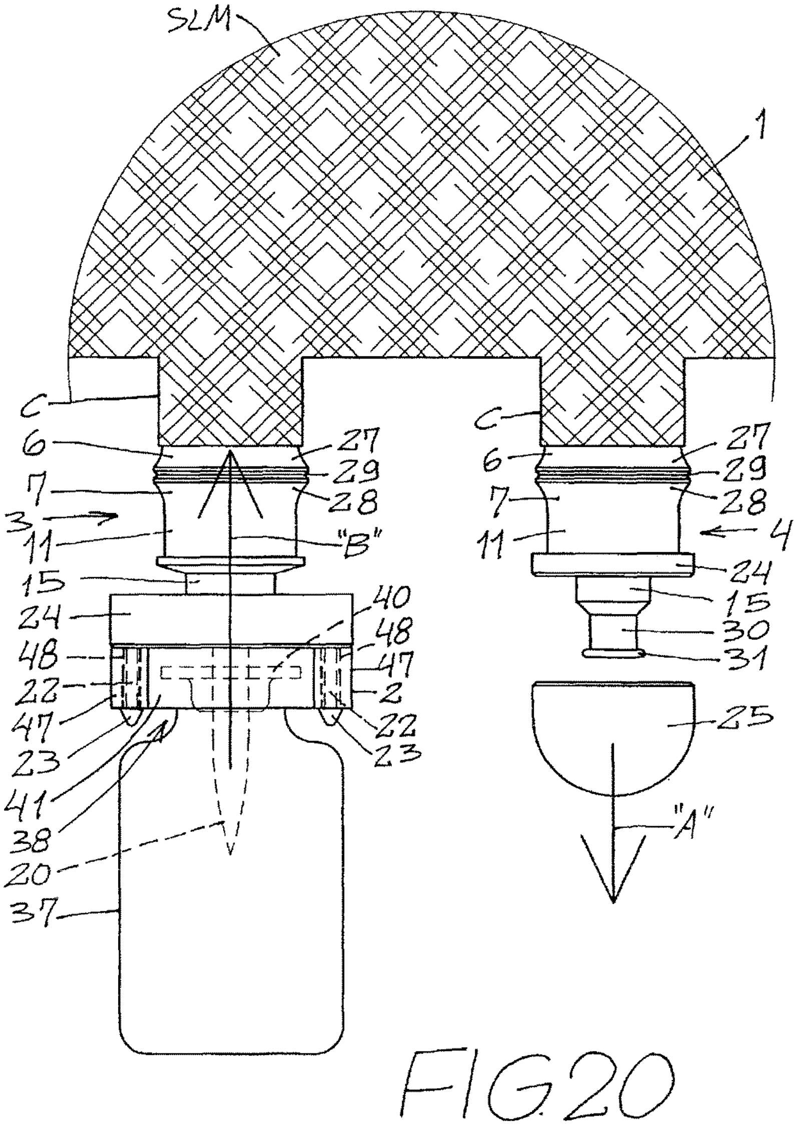
Figure 21:
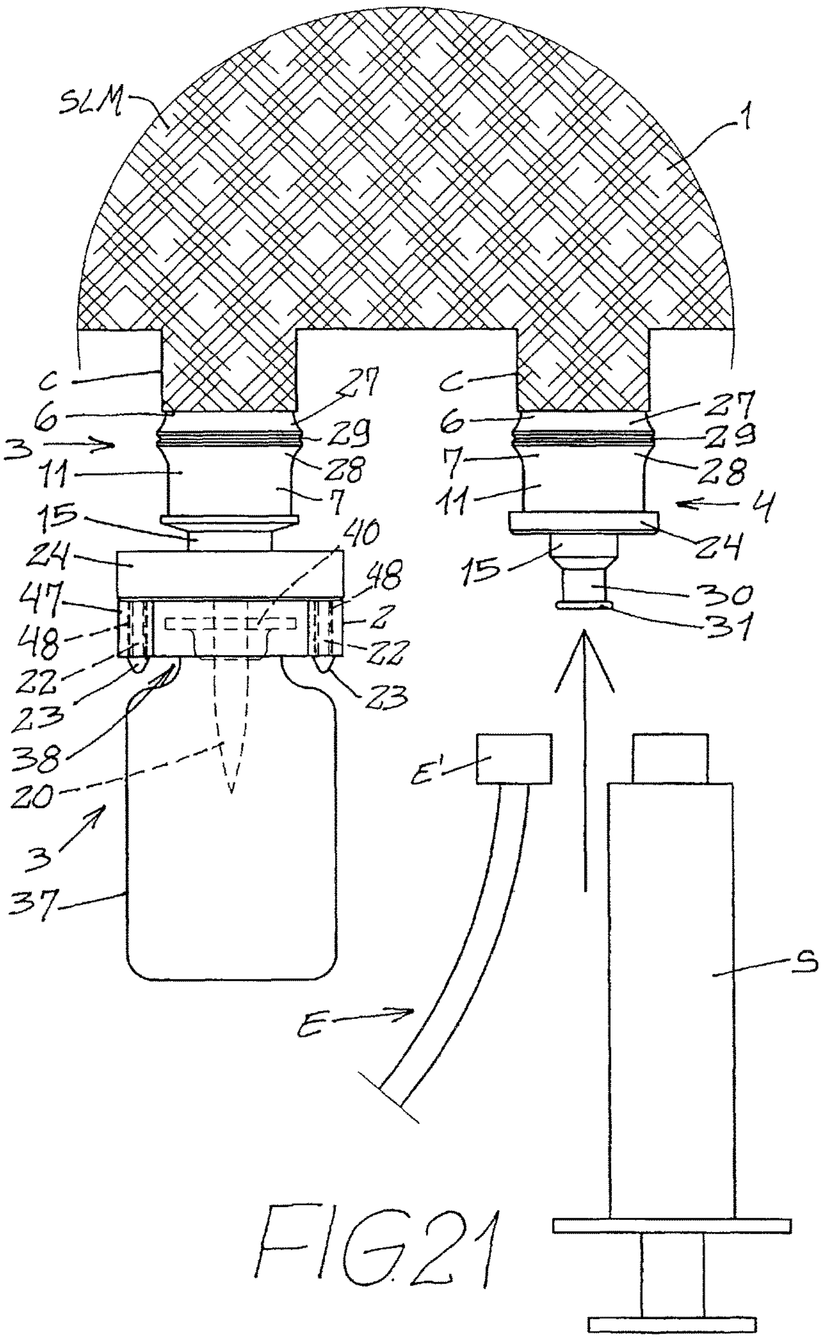
Figure 22:
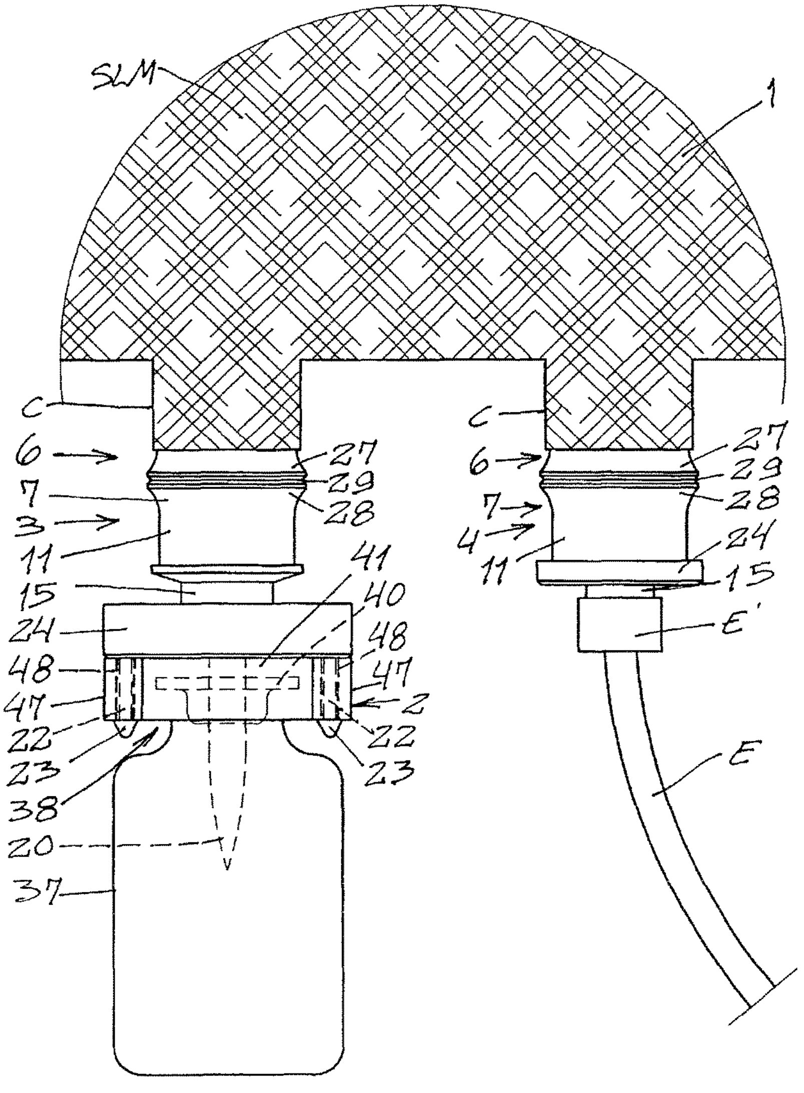
Figure 22A:
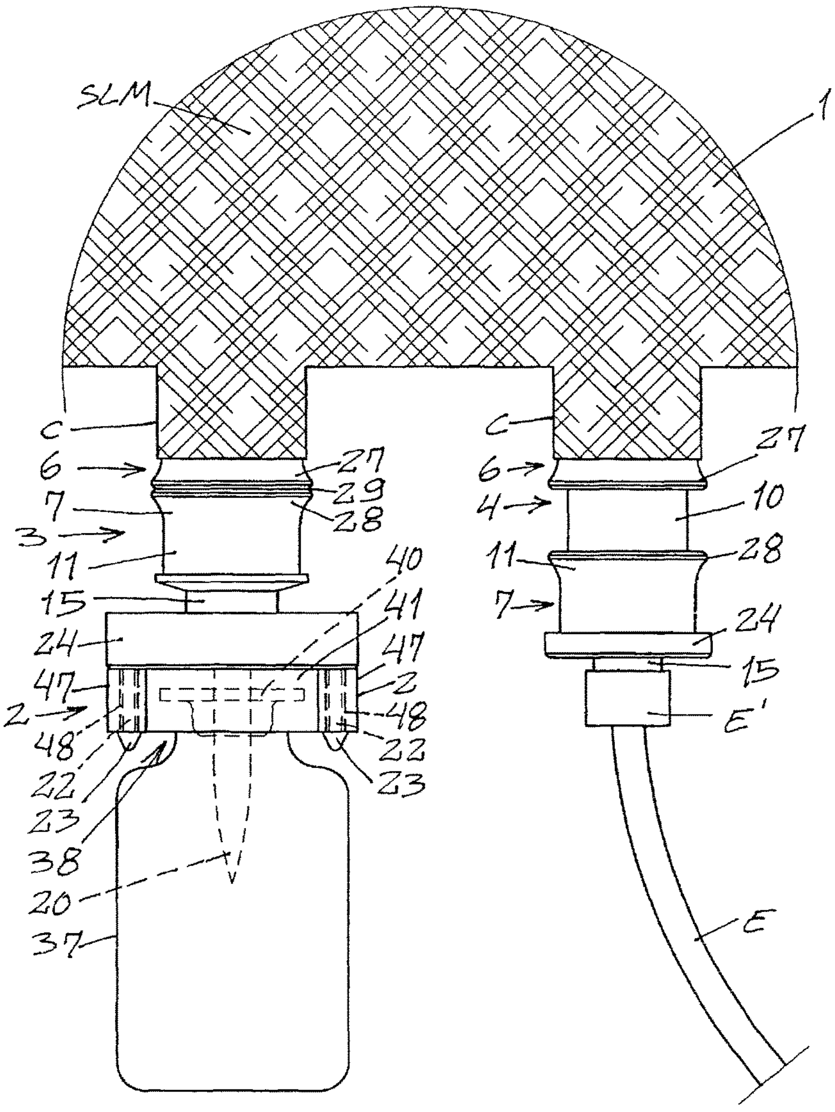
Figure 23:
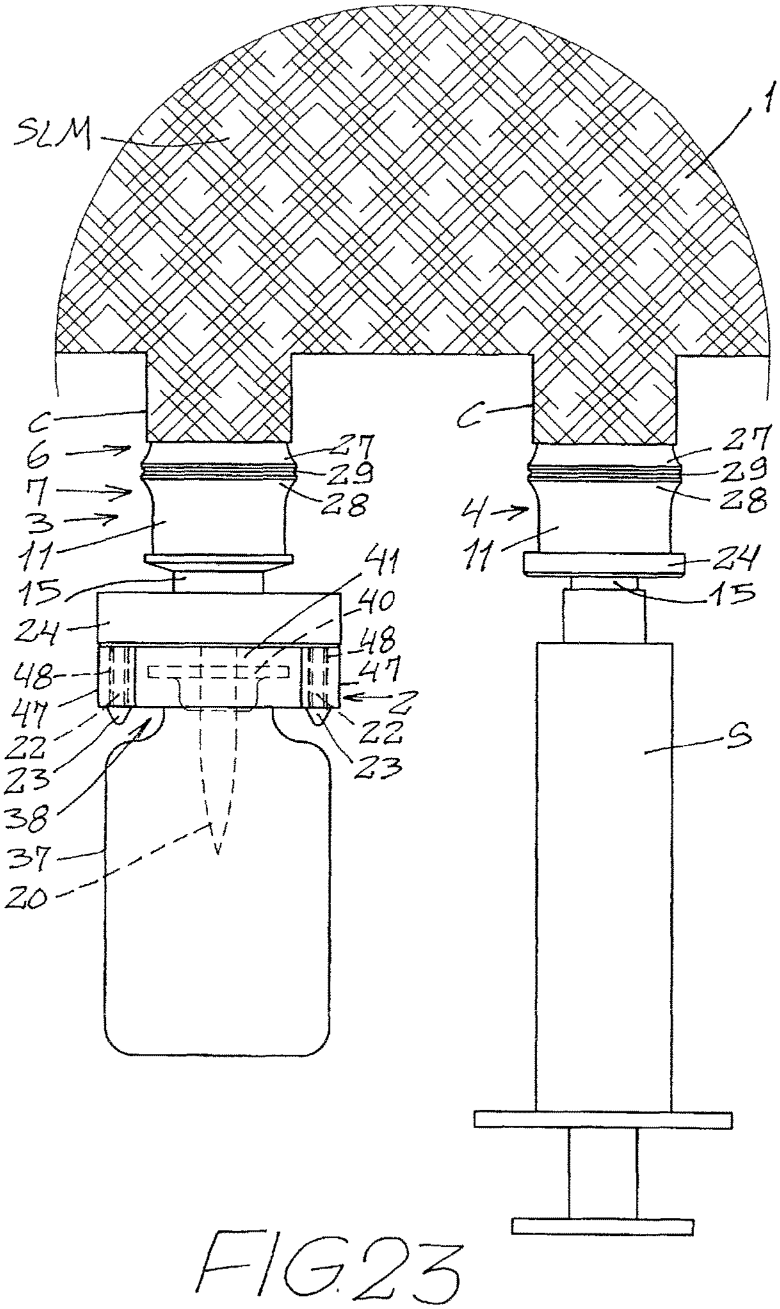
Figure 23A:
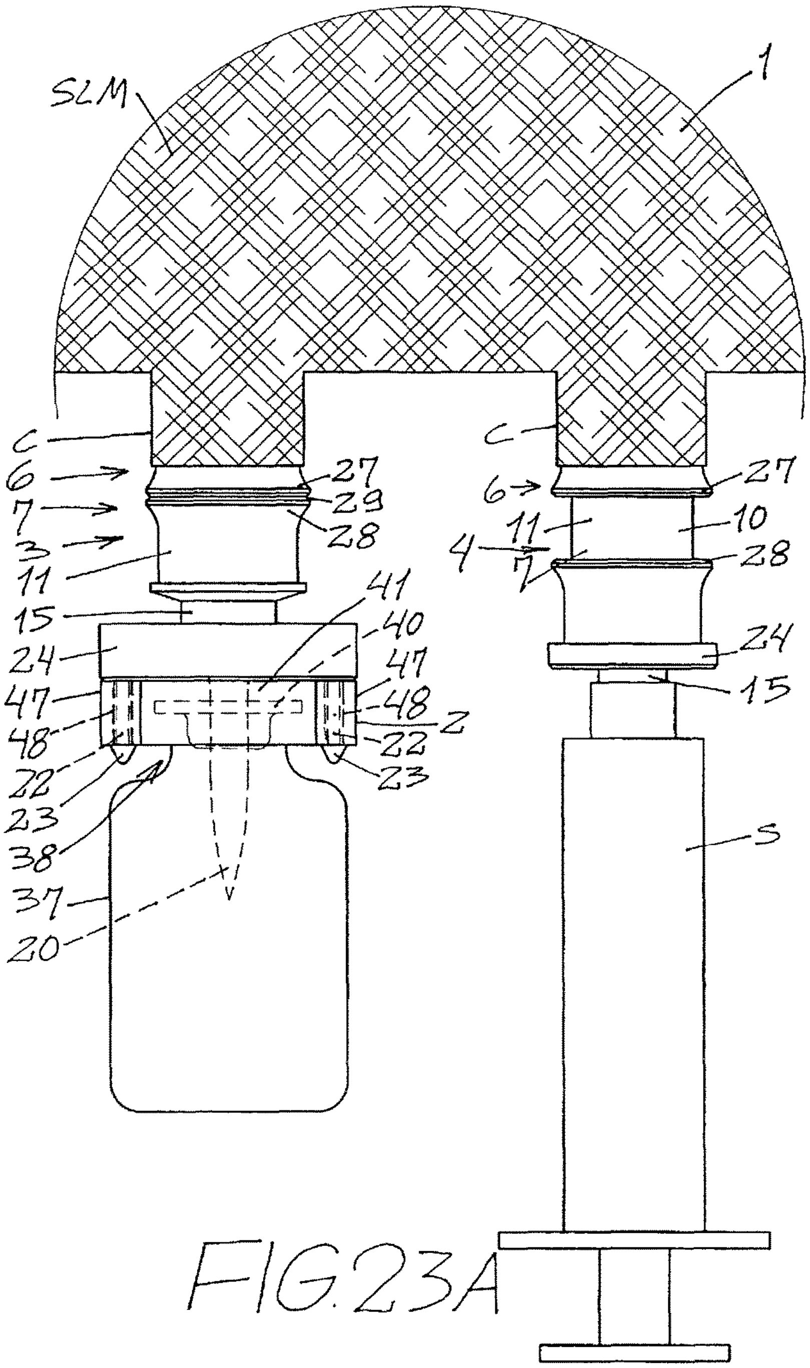
Figure 24:
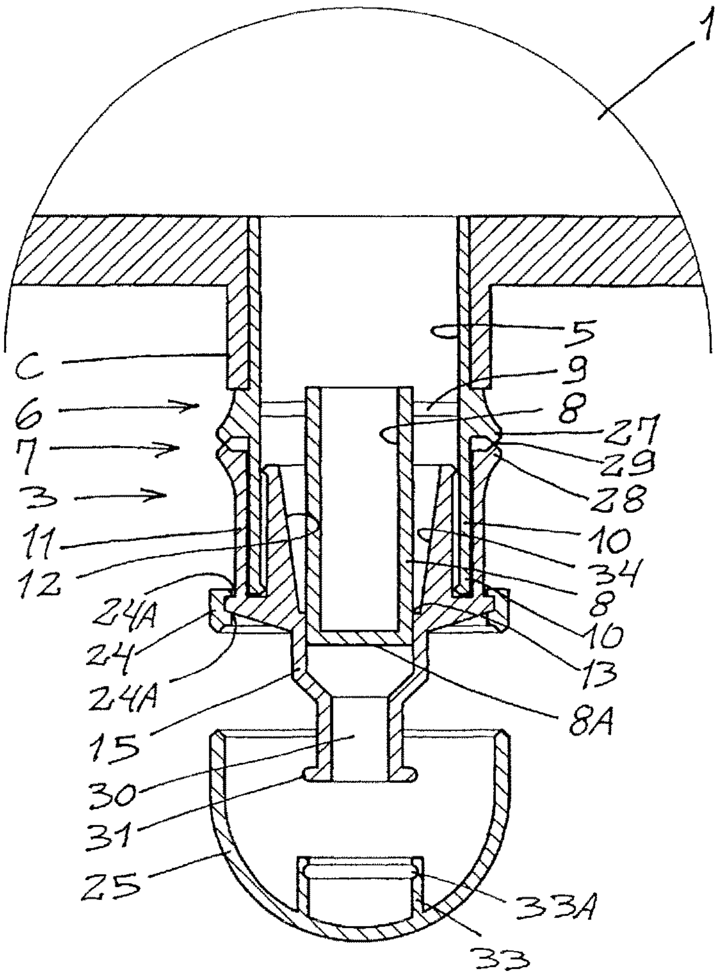
Figure 24A:
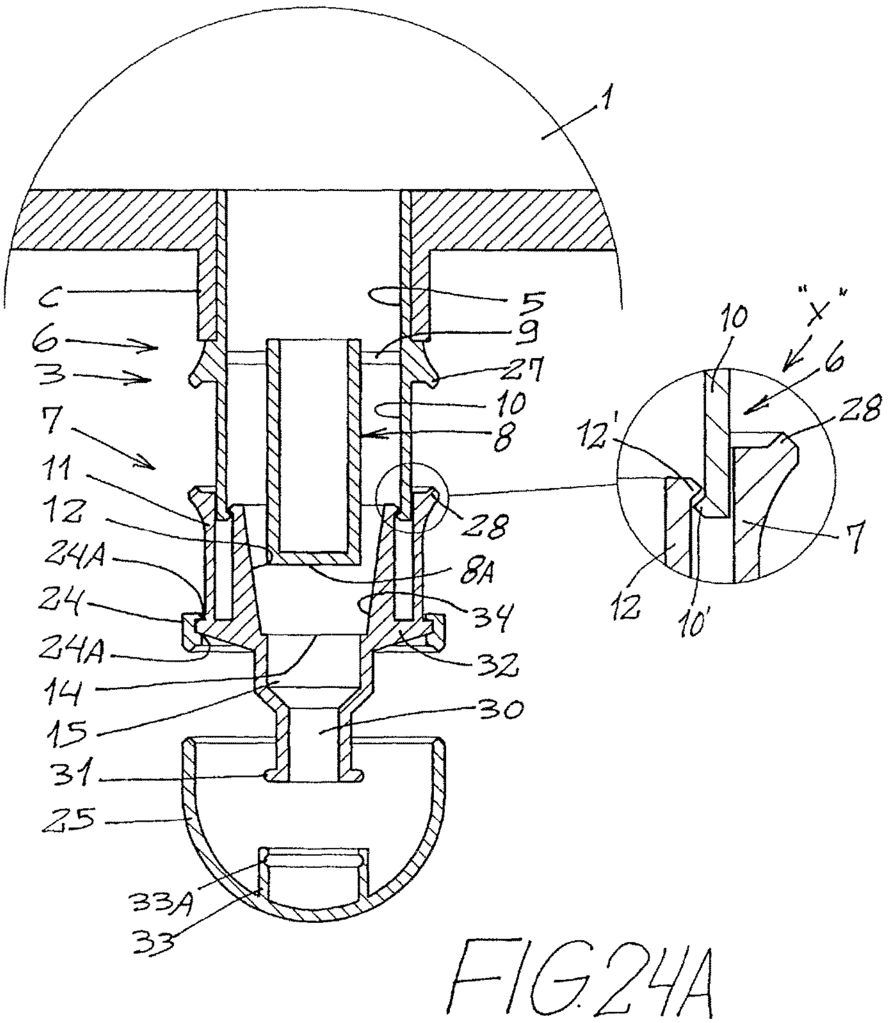
Figure 25:
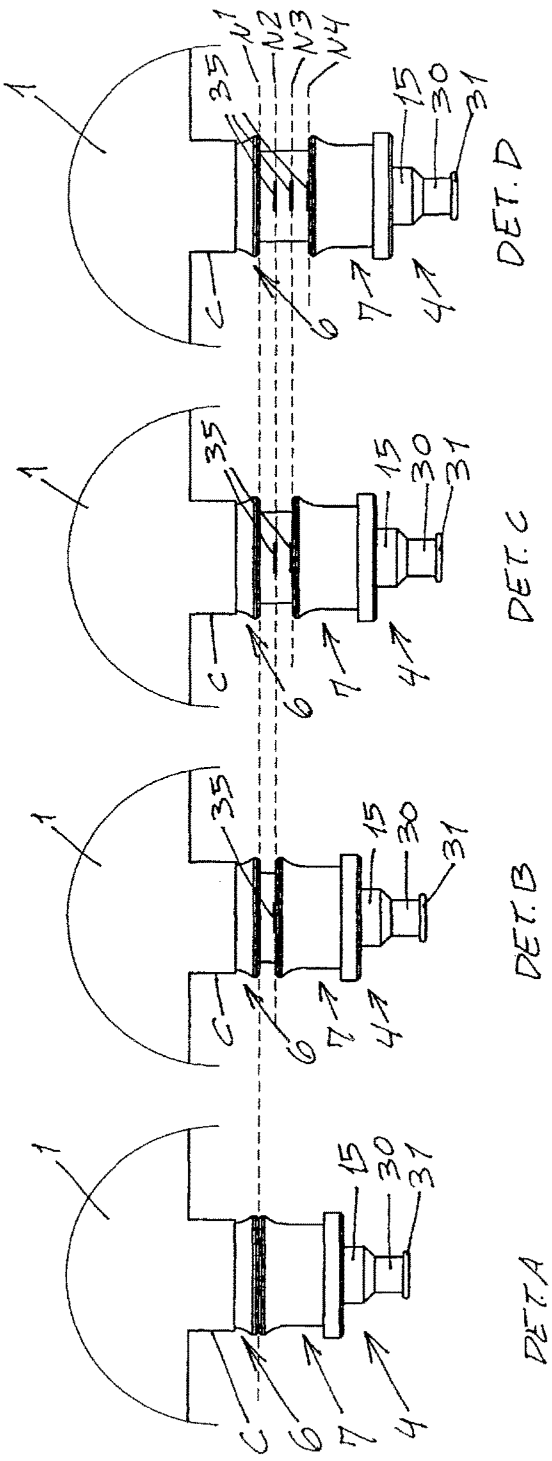
Figure 26:
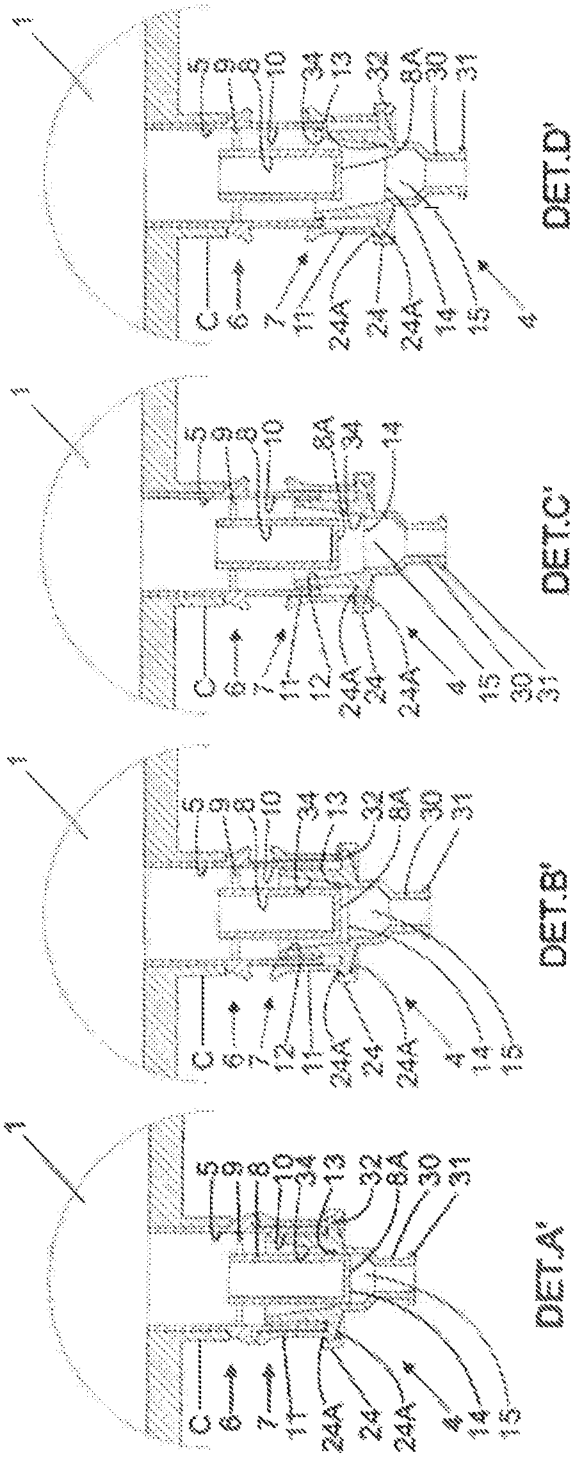
Figure 27:
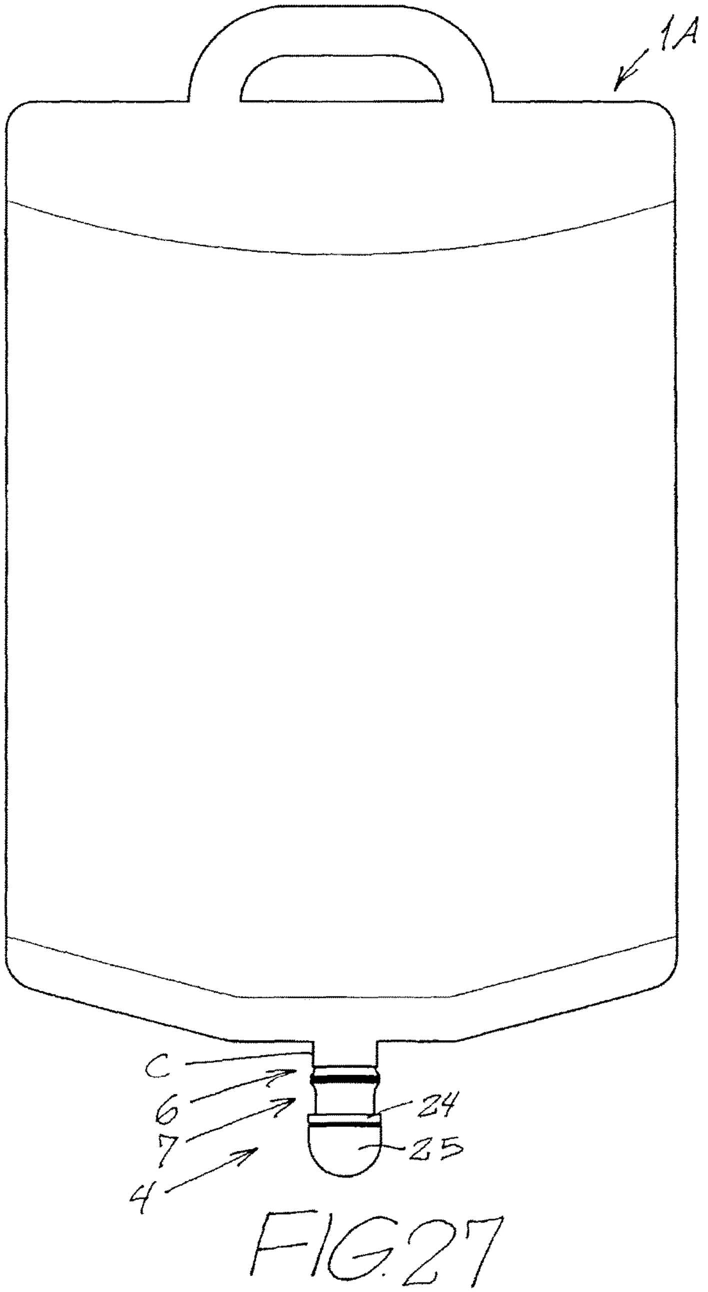

FIG. 10 shows one view similar to that shown in FIG. 9, exhibiting, however, an input door of the bag in question in its open condition and with its sealing mean already broken, as the motion indicated by the arrow "A" shows; said view shows further the spike protection lid duly separated from the assembly, such as the one indicated by the arrow "B", as well as includes one expanded detail indicated by the arrow "X", which is related to the means that promote the displacement limitation of two of said door components;

FIG. 11 shows one view in full section of the output door which is integral part of the bag model here discussed, said output door is represented in its closed condition and with its sealing means still intact;

FIG. 12 shows one view similar to that shown in FIG. 11 exhibiting, however, an output door of the bag in question with its sealing mean already broken, as the motion indicated by the arrow "A" shows, said view shows further the protection lid of the luer lock output connection duly separated from the assembly, such as the one indicated by the arrow "B", as well as includes one expanded detail indicated by the arrow "X", which is related to the means that promote the displacement limitation of two of said door components;

FIG. 13 shows a general view of the lower portion of the bag here presented, where the input and output doors of the same can be seen, as it occurs in the condition preceding the practical utilization of the bag in question;

FIG. 14 shows the practical utilization initial phase of the bag here described, stage which comprises initially the lid removal which protects the region where its spike is positioned, and the removal direction of said lid is indicated by the arrow "A";

FIG. 15 shows the position related to one generic model of a bottle containing a medicament previously fitted with one exemplary safety device, which is also proposed by the present patent, and the assembly formed by the bottle and safety device is attached and locked to the bottle bottleneck;

FIG. 16 shows one view which shows the attachment between the generic model of the bottle containing a medicament previously fitted with one exemplary safety device next to the input door of the bag here discussed, such as the one indicated by the arrow "A", attachment which occurs in one locking condition which hinders later removal of said bottle containing a medicament;

FIG. 16A shows one view in schematic section taken of FIG. 16, which shows the attachment and locking of one bottle containing a medicament previously fitted with one exemplary safety device here proposed, and the input door of one exemplary bag here discussed;

FIG. 17 shows the occasion when the input door of the bag in question is opened after bottle attachment to its spike, and the opening motion is indicated by the arrow "A", while arrow "B" indicates the input door tubular portion which remains exposed after such opening condition;

FIG. 18 shows schematically the communication between the medicament contained in the bottle and the liquid contained in the bag, communication condition which may be used to make viable the reconstitution, such as the medicament dilution, allowing thus the mutual transfer of such liquid from one mean to another, as indicated simultaneously by the arrows "A" and "B", and the liquid motion is reached through hand pressure made on the bag walls;

FIG. 19 shows one view showing the reconstitution and/or dilution process;

FIG. 19A shows the end of reconstitution and/or dilution operation of the medicament contained originally in the generic model of the bottle containing a medicament attached to the bag, and this FIG. particularly shows the final transfer of the bottle substance to the bag, as schematically signaled by the arrow "A", and the input door here shown open will be closed at the end of the process;

FIG. 20 shows the lid removal occasion from the output door of the bag here discussed, and said lid removal occasion is indicated by the arrow "A", such operation is carried out after the input door is closed again, such as the one indicated by the arrow "B", to avoid product return to the bottle;

FIG. 21 shows schematically and simultaneously both possible utilization conditions of the output door of the bag here discussed, in which the first utilization condition allows an infusion equipment attachment (which will require one luer lock attachment), of which only the end attached to the output door is shown, while the second utilization condition allows the connection of one hypodermic syringe equally with luer lock tip;

FIG. 22 shows specifically the attachment condition of one infusion equipment next to the output door of the bag here described, and said output door is in its closed condition;

FIG. 22A shows specifically the attachment condition of one infusion equipment next to the output door of the bag here described, and said output door is in its open condition;

FIG. 23 shows specifically the attachment condition of one hypodermic syringe with luer lock tip next to the output door of the bag here described, and said output door is in its closed condition;

FIG. 23A shows specifically the attachment condition of one hypodermic syringe with luer lock tip next to the output door of the bag here discussed, and said output door is in its open condition;

FIG. 24 shows one construction variant of the output door of the bag here discussed, which counts on outflow control means specially designed to allow the establishment of outflow amounts previously set of the liquid drained from inside the bag, said output door is shown in its total closure condition, only the protection lid is shown distant for better system visualization;

FIG. 24A shows a constructive variant of the output door of the bag shown in FIG. 23, said output door is shown in its condition of total opening, and includes one expanded detail indicated by the arrow "X", which is related to the means promoting the displacement limitation of two components of said door;

FIG. 25 shows schematically one detail sequence of the constructive variant of the output door of the bag here discussed, details showing stages which exhibit respectively the output door fully closed, condition represented by detail "A", while details "B" and "C" correspond to intermediate positions or stages, while detail "D" corresponds to the position or stage in which the output door is fully open;

FIG. 26 shows schematically one detail sequence of the constructive variant of the output door of the bag here discussed, such details indicated as "A'", "B'", "C'" and "D'", showing in section and in total match with details "A", "B", "C" and "D" of FIG. 25, respectively, the same stages of the output door, where the same is shown fully closed, condition represented by detail "A'", while details "B'" and "C'" correspond to intermediate positions or stages, while detail "D" corresponds to the position or stage in which the output door is fully open; and FIG. 27 shows schematically one constructive variant of the bag here proposed, which is sized to act as means of bottling of an amount of liquid substance to be used in its total volume or in a fractioned manner, said variant, in a way different from that verified in the main model, owns only a single route of access represented by an output door similar to that shown in full section in FIG. 11 or it may be the constructive variant shown in section in FIG. 24, to allow in this case the controlled drainage of the liquid contained in the bag in question.

According to what is shown in the figures above listed, the bag for conditioning, reconstitution and/or dilution of injectable products here presented is indicated generically by the numeric reference 1.

The bag 1 here proposed comprises one main model, which is shown in FIGS. 1, 3, 4, 9-26, and sets forth further one constructive variant indicated by the reference 1A, which is specifically shown in FIG. 27.

In addition to the bag above mentioned, the present patent of Invention Privilege proposes also one safety device intended to be used along with the same, which is indicated specifically by the reference 2.

The safety device 2 is intended to be applied to the bottleneck of any bottle containing a medicament which may be attached to the bag 1, acting in order to prevent said bottle from being later unattached after being attached to the bag 1.

Specifically in relation to the main model of bag here shown and which is indicated by the reference 1, this comprises two routes of access called doors, it being one an input door 3 and another an output door 4.

Figure 1:
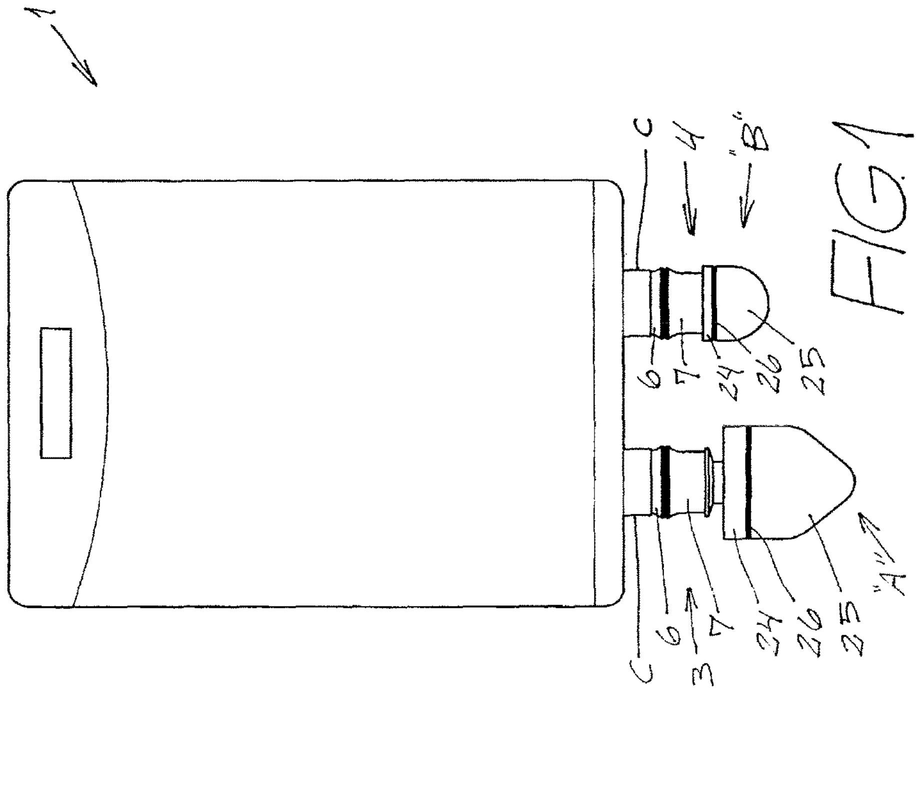
FIG. 1 shows a general view of the bag here discussed.
Figure 3:
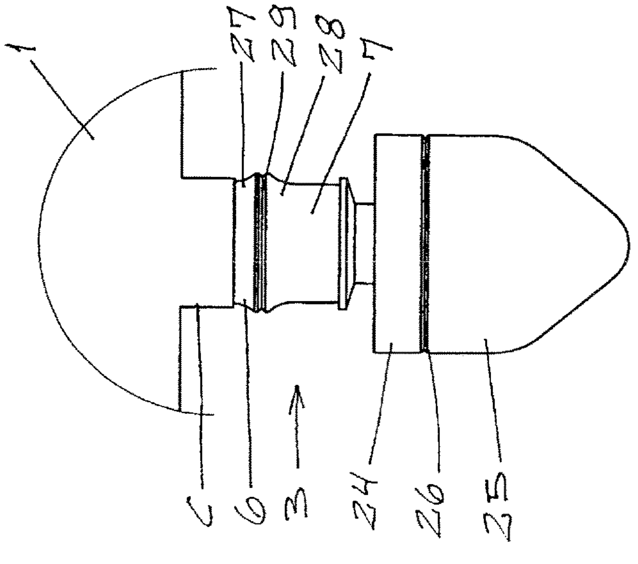
FIG. 3 shows an expanded detail of the bag here presented, which is taken from FIG. 1, such as the one indicated by the arrow "A"

The input door 3, such as the one indicated by the arrow "A" of FIG. 1 and also in relation to what is shown in FIGS. 3, 9 and 10, consists of a tube sector 5 incorporated to the plastic tube C provided for the lower edge of the bag 1 structure, said tube sector 5 constitutes a full extension of an obturator 6, which is complemented by a mobile connection 7.

The obturator 6 is fitted with a central projection 8 linked to the structure of said obturator by one set of radial arms 9, said central projection 8 is basically assembled internally in a tubular sector 10 which is an extension of the tube sector 5 and acts as means of assembly for the mobile connection 7.

The mobile connection 7 encompasses the obturator 6 through a surrounding tubular wall 11 and an internal tubular projection 12, as it can be better understood by observing FIG. 9.

The mobile connection 7 is internally fitted with a closure wall 13, which is centrally fitted with a circular opening 14 sized in its diameter to be totally obstructed by the end 8A of the central projection 8 incorporated to the obturator 6.

The mobile connection 7 presents in its lower portion one route of communication 15 in a chamber 16 occupied by one filtering element unit 17, said chamber presents one route of passage 18 which continues in one tubular body 19 which configures the spike 20 structure.

The mobile connection 7 structure where the filtering element 17 is internally placed and which is indicated by the reference 7A presents a basically circular configuration, retention pins 22 emerge mutually in parallel from the lower face 21 of such structure lower face 21, each pin incorporating a crack-like terminal 23 in its free end.

One ring 24 is assembled around the circular structure 7A of the mobile connection, ring which is integral part of one protection lid 25, which covers both the spike 20 and the retention pins 22.

The ring 24 presents outlining edges 24A, which are sized to produce tight grasp of the same around the circular structure 7A of the mobile connection 7, detail which causes said ring 24 to remain attached around the circular structure 7A of the mobile connection 7 even after removal of the lid 25.

Between the ring 24 and the lid 25 a weakening line 26 is created, which acts as breaking point to allow the separation of the protection lid 25 upon effective use of the bag 1.

Further about the obturator 6, such presents also an annular edge 27, which is sized to maintain one overlaying in relation to one annular edge 28 incorporated to the upper end of the mobile connection 7, thus creating one perimetric line subject to the welded or jointed to configure one breakage region 29 which acts as seal that ensures the inviolability of the bag 1, such as that verified also in relation to the weakening line 26 which separates the ring 24 from the protection lid 25.

The input door 3 thus defined constitutes one mean of access to the liquid contained in the bag 1, liquid which can only be handled if both sealing above described are broken, that is, the weakening line 26, which is integral part of the lid structure 25 and the breakage region 29, which establishes the link between the mobile connection 7 with the obturator 6 structure.

The input door 3 may be viewed in section in FIG. 9 in its fully closed condition, while in FIG. 10 the same input door 3 may be viewed in its total opening condition, that is, with its lid 25 separated and further with the mobile connection 7 fully displaced in relation to the obturator 6.

Specifically in relation to what is shown in FIG. 10, it may be noticed that the central projection 8, which is integral part of the obturator 6 structure, is fully put away from the circular opening 14 provided in the closure wall 13 of the mobile connection 7, such fact corresponds to the total input door 3 opening.

In the condition shown in said FIG. 10, the liquid contained inside the bag 1 may be poured out and then in of said bag, through the hand pressure movements on the bag walls, as must occur as a result of reconstitution and/or dilution procedures.

In the same FIG. 10, it may be noticed, through the expanded detail indicated by the arrow "X", that means of interference are not provided between the tubular sector 10 and the internal projection 12, such means represented by an annular projection 10' which integrates the obturator 6 and a corresponding annular projection 12', which integrates the internal tubular projection 12, said annual projections are sized and positioned to prevent the total separation of obturator 6 and mobile connection 7, limiting further the mutual displacement between both.

Figure 4:
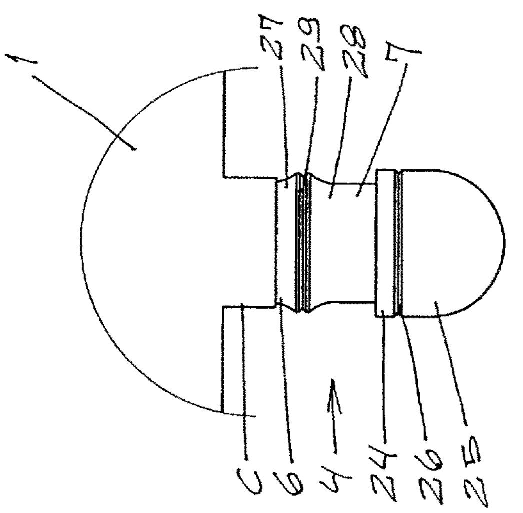
FIG. 4 shows an expanded detail taken of the bag object of this patent of Invention Privilege, said detail being indicated in FIG. 1 by the arrow "B"

The bag 1 here proposed is further fitted with the already mentioned output door 4, which, such as the one indicated by the arrow "B" of FIG. 1 and also in relation to what is shown in FIGS. 4, 11 and 12, consists of another tube sector 5, which, as occurs with the tube sector 5 integral part of the input door 3, is incorporated to another plastic tube C provided in the lower edge of the bag 1 structure.

The output door 4 presents many components common with the input door 3, which are indicated by the same numeric references.

Thus, the output door 4 incorporated to the lower edge of the bag 1 structure of the already mentioned tube 5, which receives the tight assembly of an obturator 6, which is complemented by the mobile connection 7.

The obturator 6 of the output door 4, such as that verified in relation to the input door 3, is fitted with one central projection 8, which is linked to said obturator structure 6 by one set of radial arms 9, said central projection 8 is basically assembled internally in a tubular sector 10 which acts as mean of assembly for the mobile connection 7.

Both the obturator 6 and the mobile connection 7 are components designed to allow mutual assembly of the same, whereas provided that the tubular sector 10 of the obturator 6 is sized to be fitted inside the mobile connection 7, lying between the tubular and outlining wall 11 of the same and one internal projection 12 equally of tubular profile.

The mobile connection 7 of the output door 4 is fitted internally also, similar to what is verified in relation to the input door 3, with a closure wall 13, which is centrally fitted with a circular opening 14 sized in its diameter so it can be totally obstructed by the end 8A of the central projection 8 incorporated to the obturator 6.

The mobile connection 7 of the output door 4 presents a tubular extension 15, which, differently from what is verified in relation to the input door 3, suffers a diameter reduction 30, which is fitted, for example, with on luer lock attachment terminal 31.

A ring 24 is assembled around an edge 32 provided in the mobile connection 7, which is integral part of a protection lid 25 which covers the luer lock terminal 31.

The ring 24 which ensures the lid 25 positioning in order to protect the output door 4 presents, such as what is verified in relation to the ring 24 integral part of the lid 25 which covers the input door 3, outlining edges 24A, which are sized to produce tight grasp of the same around the edge 32 of the mobile connection 7.

Further similar to what is verified in relation to the input door 3, also in case of the output door 4, the ring 24 is assembled so that the same remains jointed around the mobile connection 7 even after the separation of its respective lid 25.

One weakening line 26 is created between the ring 24 and the lid 25 of the output door 4, similar to what is verified in relation to the input door 3, line which acts as breakage point to allow the separation of the protection lid 25 during the effective use of the bag 1.

Further about the obturator 6 of the output door 4, the same presents also an annular edge 27 which is sized to maintain an overlaying position in relation to an annular edge 28 incorporated to the upper end of the mobile connection 7, thus creating one perimetric line subject to be welded or jointed to configure a breakage region 29 which acts as a seal in order to ensure the inviolability of the bag 1, such as what is verified also in relation to the weakening line 26 which separates the ring 24 from the protection lid 25.

In relation to the protection lid 25 integral part of the output door 4, the lid differs from its congener which is integral part of the input door 3 only in its sizing and also by the fact that internally is fitted with a projection 33 equipped with an internal annular lowering 33A, which is sized to receive the luer lock terminal 31 fit, fact which allows that said lid 25, differently from its congener integrating the input door 3, may be positioned again next to the output door 4 even after breakage of its weakening line which acts as seal, working as additional safety to prevent contact with the output terminal.

The output door 4 thus defined constitutes one mean of liquid outflow which is contained in the bag 1, liquid which can only be handled if both sealing means above described are broken, that is, the weakening line 26 which integrates the lid 25 structure and the breakage region 29 which establishes the link between the mobile connection 7 with the obturator 6 structure.

The output door 4 may be viewed in section in FIG. 11 in its fully closed condition, while in FIG. 12 the same output door 4 may be viewed in its fully open condition, that is, with its lid 25 separated and obturator 6.

In the same FIG. 12 it may be observed, through the expanded detail indicated by the arrow "X", that in relation to the output door 4 and the similarity of what is verified in respect to the input door 3, means of interference are provided between the tubular sector 10 and the internal tubular projection 12, such means represented by an annular projection 10' which integrates the obturator 6 and a corresponding annular projection 12', which integrates the internal tubular projection 12, said annular projections are sized and positioned to prevent the total separation of obturator 6 and mobile connection 7, limiting further the mutual displacement between both.

The output door 4 presents one constructive variant which is particularly shown in FIGS. 24 and 24A and which operation is particularly shown in details of FIGS. 25 and 26.

The variant of the output door 4 shown in FIGS. 24 and 24A differs from the original model above described only in order to allow, through a simple adjustment, that said output door 4 itself may be used as mean of outflow control to establish thus standards previously defined of outflow speed of the liquid contained inside bag 1, condition which is particularly useful to help the administration rate of the liquid contained in bag 1 directly to the patient, where an infusion equipment is invariably used.

The output door 4 which constitutes the constructive variant shown in FIGS. 24 and 24A presents the internal profile of its mobile connection 7 defined by an essentially truncated-cone shaped wall 34, which establishes different outflow levels due to the relative positioning between the end 8A of the projection 8 integral part of the obturator 6 and the circular opening 14 which is centrally incorporated to the closure wall 13 of the mobile connection 7.

Thus, as long as the mobile connection 7 is pulled down, the liquid flow that passes inside the same is changed as a result of bigger or smaller choke of the passage established by the relative positioning of end 8A of said projection 8 and the circular opening 14.

For such reason, the output door 4 defined according to the variant shown in FIGS. 24 and 24A starts playing a secondary function which is to allow the control of dosage administered to the patient per time unit.

Such condition may be particularly understood through joint observation of details which integrate FIGS. 25 and 26.

FIG. 25 exhibits the representation of four stages of the constructive variant of the output door 4, where detail "A" corresponds to the total closure of the same; the details "B" and "C" correspond to two different opening levels, which establish two equally different levels of outflow; and detail "D" corresponds to the total opening stage of the output door 4.

The four stages above described are related to the positioning and also the displacement of the mobile connection 7 in relation to the obturator 6, and such displacement may be quantified by markers 35 which are integrated to the external wall of the tubular sector 10 of said obturator 6.

The details "A", "B", "C", and "D" of FIG. 25, when observed jointly, allow the verification of position level establishment for the mobile connection 7, as it can be accompanied by the lines of level N1, N2, N3, and N4.

The obtainment of four stages above presented, which start with the total closure of the output door 4 and culminate with the total opening of the same, going through two intermediate stages, may be better understood through the observation of FIG. 26.

FIG. 26 is a section reproduction of the constructive variant of the output door 4 of FIGS. 24 and 24A in each of the stages reproduced in FIG. 25.

Thus, FIG. 26 shows the representation of four stages of the output door 4, where detail "A'" corresponds to the total closure of the same; details "B'" and "C'" correspond to two different opening levels, which establish two equally different levels of outflow; and detail "D'" corresponds to the total opening stage of the output door 4 obtained according to the constructive variant mentioned.

Still in respect to the constructive variant of the output door 4 shown in FIGS. 24 and 24A, it may be noticed, in FIG. 24A, through the expanded detail indicated by the arrow "X", that similarly to what is verified in respect to the main model of the output door 4 or even in relation to the input door 3, that means of interference are provided between the mobile connection 7 and the obturator 6, such means represented by an annular projection 10' which integrates the obturator 6, and a corresponding annular projection 12', which integrates the internal tubular projection 12, said annular projections are sized and positioned to prevent the total separation of obturator 6 and mobile connection 7, limiting further the mutual displacement between both.

The description presented above allows knowing the full bag 1 design, mode of utilization of the same will be presented in relation to what is shown in FIGS. 13 to 23A.

Figure 2:
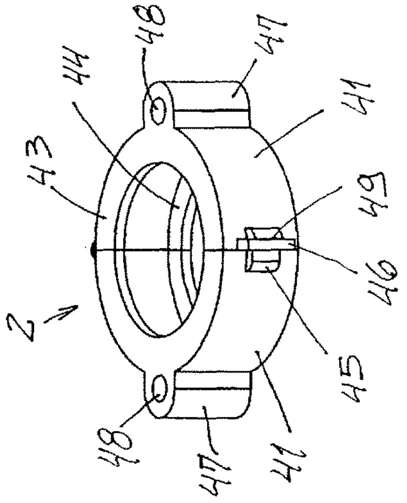
FIG. 2 shows an isolated view and in perspective of the safety device which is used jointly with the bag here presented, and said safety device is in its total closure condition.
Figure 6:
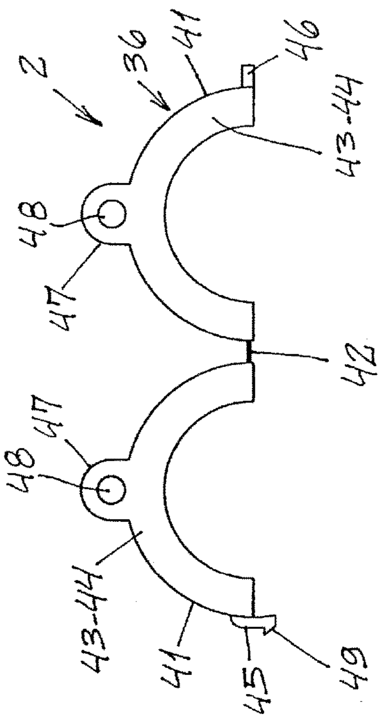
FIG. 6 shows one view of said safety device, which is shown in its condition of total opening.
Figure 5:
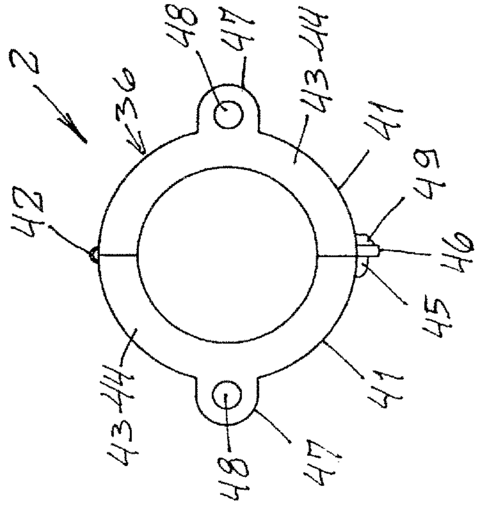
FIG. 5 shows one view of the safety device presented in FIG. 2, which is specially shown in plain view and in its total closure condition.

Another item by this patent of Invention Privilege is the safety device 2, which is shown in separate in FIGS. 2, 5, 6, attached to the bottle in FIG. 7 and in section attached to the bottle in FIG. 8.

The safety device 2 is intended to be attached to a bottle containing a medicament 37, whereas retained more specifically in the region of the bottleneck 38 of the same, involving also the whole periphery of its closure metallic ring 39, leaving exposed the upper portions of such metallic ring 39 and also the portion of the rubber cork 40 that seals the bottle 37.

The safety device 2 acts similarly to handcuffs, whereas defined as a single-block piece 36 obtained preferably in injection molded plastic and fitted with two complementary sections indicated by the reference 41, interlinked by one joint rim 42 which acts similarly to a full hinge.

The two complementary sections 41 may then present a relative opening and closure motion which is provided for by the material flexibility of which the safety device 2 is produced and in particular by the combination of such flexibility with the condition represented by the measure of reduced thickness which characterizes the joint rim 42.

The complementary sections 41 present involving rims 43 and 44 which establish the tight settlement of the safety device 2 in relation to the profile of the bottleneck 38 of the bottle 37 and more specifically in relation to the region covered by the metallic ring 39 which causes the cork 40 attachment in relation to the nozzle of said bottle 37.

The safety device 2 is fitted with locking means represented by a retention projection 45 which integrates and is located in the end of one of the complementary sections 41, which is sized and laid in order to be inserted into a retention handle 46 incorporated to the end of another complementary section 41, and such insertion condition occurs upon closure of said safety device 2, as particularly shown in FIGS. 2, 5, 7, and 8.

The safety device 2 incorporates further, in each of the complementary sections 41, a side projection 47, each fitted with a channel 48.

Once assembled around the bottleneck 38 of the bottle 37 and after the retention projection 45 has been inserted into its corresponding retention handle 46, the ramped tooth 49 of the retention projection 45, after passing by the opening of the retention handle 46, prevents that said retention projection 45 might be withdrawn, fact which establishes the irreversible closure of lock device 2 around the bottleneck 38 of the bottle 37.

Such irreversible closure effect, such as shown in FIGS. 7 and 8, will be extremely important in the utilization system of the bag 1 here discussed, since it will prevent that a bottle containing a medicament 37, after connected to the input door 3, is unduly removed.

The practical utilization of the bag 1 and safety device 2 associated to the same may be understood from what is shown in FIGS. 13 to 23.

Specifically in relation to what is shown in FIG. 13, it may be observed that the same shows a general view of the lower portion of the bag 1 here presented, where the input 3 and output doors may be seen, said view includes further a specific hatching patter to indicate the presence of a liquid substance (LS) not handled inside the bag 1.

In the same FIG. 13, it may be observed that both in relation to the input door 3 and also in respect to the output door 4, the corresponding protection lids 25 are still intact as well as the respective links between the obturators 6 and their corresponding mobile connections 7.

The practical utilization start of the bag 1 occurs by removing the lid 25 of the input door 3, operation which exposes both the spike 20 and the retention pins 22, as it can be verified by observing FIG. 14 where the separation of the lid 25 of the input door 3 is schematically indicated by the arrow "A".

FIG. 15 shows the relative positioning of a bottle containing a medicament 37 previously fitted with one exemplary safety device 2, whereas such positioning is done in order to align the retention pins 22 with the channels 48 of the side projections 47 provided in the complementary sections 41 of the safety device 2 assembled around the bottleneck 38 of said bottle 37, whereas said retention pins 22 serve also as guide requiring the spike 20 to puncture the cork 40 in a perpendicular line, diminishing the particle generation possibility (called "coring"), which anyhow will be fitted with the retention through the filtering element 17 associated to the spike 20.

The positioning above described establishes also that the spike 20 is aligned with the cork core 40 of the bottle 37 and the spike remains in such position in order to proceed to the cork puncture.

The motion establishing the bottle 37 attachment to the input door 3 is indicated by the arrow "A" of FIG. 16.

The same FIG. 16 shows that the safety device 2 established one irreversible locking condition in relation to the input door 3, since the crack-like terminations 23 of the retention pins 22 exceeded the limits of the respective channels 48 incorporated into the side projections 47 of each of the complementary sections 41 of the device 2, thus preventing the separation of said safety device 2 and as a consequence it prevents also the separation of the bottle 37 attached to the same, thus ensuring the easy medicament identification which will be reconstituted and/or diluted.

The locking condition above described may be better viewed in FIG. 16A, which is the section representation of the input door 3 such as represented in FIG. 16.

The same FIG. 16A shows further, by means of specific hatching, both the liquid substance LS not manipulated yet inside the bag 1, and the medicament M contained inside the bottle 37.

It may be observed that the bottle 37 shown in FIG. 16, such as what is verified also in relation to its representation in FIG. 15, presents a hatching pattern representing a substance M (medicament) not manipulated yet, whether by reconstitution or further by dilution.

FIG. 17 shows the occasion when the input door 3 of the bag 1 in question is opened, motion which is indicated by the arrow “A” which corresponds to the downwards displacement of the mobile connection 7 in relation to the obturator 6, which starts exposing the external wall of its tubular sector 10.

FIG. 18 shows schematically the communication between the medicament M contained inside the bag 37 and liquid substance LS contained inside the bag 1, whereas such communication allows the mutual transference of the liquid substance LS from one mean to another in order to promote the reconstitution and/or dilution of medicament M contained in the bottle 37.

The reconstitution and/or dilution systematic follows the procedures conventionally used in the medical area, through the observance of aseptic techniques and hand pressure motions onto the bag walls, reason why one detailed explanation about such technique is not necessary.

It is worth stressing out that the liquid substance LS touches the filtering element 17 only upon the transfer of such substance to the bottle 37, once that such filtering element was fully isolated and hermetically separated from the bag 1 internal environment until actual opening of the input door 3. The absence of contact between the filtering element 17 with the solution contained in bag 1 was designed to avoid requirement of new technical validations of the solution in contact with the filter which could eventually change the validity term of such solution.

The filtering element 17 is specified in order to avoid liquid substance LS flow blockage during its passage into the interior of the bottle 37, and to avoid blockage during return of said substance LS after the same touches the medicament M contained in the bottle 37, contact which is crucial for the medicament M reconstitution and/or dilution.

The filtering element 17 sole function is to prevent that eventual solid particles of the cork 40 material produced upon cork puncture by the spike 20 may be carried into the bag 1 upon medicament M transfer from the bottle 37 to the bag 1.

Objectively, the filtering element 17 establishes a barrier only for particles deriving from the coring phenomenon which eventually are generated when the cork 40 is punctured by the spike 20, or even for other foreign particles eventually present and not viewed inside the bottle 37.

FIG. 19 shows one view that shows the reconstitution and/or dilution process and FIG. 19A shows the end of the reconstitution and/or dilution operation of the medicament contained originally inside the generic model of the bottle containing a medicament attached to the bag, whereas this FIG. particularly shows the final substance transfer from the bottle to the bag, as schematically signaled by the arrow “A”, and an input door which here appears open will be closed at the end of the process.

FIG. 20 shows a bag 1 already duly filled with the liquid substance LS already added (by reconstitution and/or dilution) of medicament M, condition represented by another specific hatching pattern which is indicated by the reference SLM allusive to the incorporation (by reconstitution and/or dilution) of medicament M to the liquid substance LS.

FIG. 20 shows that the input door 3 was closed through upward dislocation of the mobile connection 7, condition indicated by the arrow “B”, fact which prevent that any portion of the bag 1 content already mixed may accidentally return to the bottle 37, thus ensuring the total utilization and without loss of the dose of medicament to be administered to the patient.

The same FIG. 20 shows further the moment when the protection lid 25 is removed from the output door 4 of the bag 1 here discussed, removal which is indicated by the arrow “A”.

The removal of lid 25, as previously explained, occurs upon breakage of the weakening line 26 which joints said lid 25 to its ring 24.

FIG. 21 shows schematically and simultaneously both possible utilization conditions of the output door 4 of the bag 1 here discussed, where the first utilization condition allows the attachment of one luer lock device infusion equipment, indicated generally by the reference E, of which only end E', connected to output door 4 is shown, while the second utilization condition allows the connection of one hypodermic syringe S with luer lock tip.

FIG. 22 shows specifically the attachment condition of one infusion equipment E to the output door 4 of the bag 1 here described, operation which is possible since both the output door 4 and also equipment E are fitted with the same connection pattern, which in the example shown, corresponds to the luer lock pattern.

FIG. 22A shows that after the equipment E attachment to the output door 4, such door may then be opened upon downward dislocation of its mobile connection 7, thus releasing the flow of substance contained in bag 1, and it must be stressed out that at any time and depending on an eventual requirement the output door 4 may be closed again in a quick and simple manner.

Inside the context of bag 1 use together with the infusion equipment E, it is worth mentioning again the constructive variant of the output door 4 shown in FIGS. 24, 25, and 26, provided that the possibility to balance the flow directly from the output door 4 for direct administration to the patient is advantageously for such utilization.

FIG. 23 shows specifically the attachment condition of a hypodermic syringe S to the output door 4 of the bag 1, also using in this case the fact that said output door 4 incorporates the luer lock terminal 31 common to the syringe S.

The possibility of direct connection of a hypodermic syringe S to the output door 4 allows that, in an innovative manner, the substance contained in bag 1 may be used in fractioned doses, without particle generation, and the output door 4 may then be closed again and protected, after the removal of each fraction, by its corresponding protection lid 25, which also makes use of the same luer lock terminal 31 to ensure its attachment.

The design solution adopted for bag 1 here presented allows that the same may be used both to serve as hermetically closed and protected environment, where reconstitution and/or dilution procedures of medicaments for direct administration to the patient may be conducted as well as it allows that in a new version of said bag 1, such bag is employed to contain a substance already prepared for use (medicament or diluent) and which may also allow that the solution is used in a fractioned form when necessary.

In this other kind of use above described, the version of bag 1, indicated specifically by the reference 1A and particularly shown in FIG. 27, does not adopt the input door 3 and, for such reason, it relies on the output door 4 only.

The non-adoption of input door 3 is explained by the fact that bag A defined according to the variant shown in FIG. 27 is primarily intended to containment of originally liquid diluents or injectable medicaments.

The solution here presented bears full practical capacity, once bag 1 (or its variant 1A), as well as the safety device 2 represent a radical change from the safety level point of view that may be provided for patient care upon injectable substance use.

Based on the above, it must be stressed out that in a comprehensive way the main factor to be taken into consideration while managing an aseptic process use is the human action on the process. Everything that can be done to ease the process and ensure a safe handling will result in safety for the patient.

It must be also taken into consideration that as regards the pharmaceutical industry, while the pharmaceutical productive process controls are extremely rigid, we live with a dangerous freedom in terms of use of materials, equipment and techniques unsuitable for reconstitution and/or dilution of injectable products. This phase of one product reconstitution for injectable use practically represents a dangerous outsourcing of such product "manufacturing process", which requires a conceptual revolution and utilization of safer equipment, as this one that we propose in this patent application.

Thus, we may assure that bag 1 here discussed (or its variant 1A) as well the safety device 2 will fully change the way we give this fundamental step of injectable product administration whether in humans or also in animals.

The invention claimed is:

1. A spike-type connector for a medicament reconstitution bag, comprising:
- an input door and an output door,
- wherein the input door comprises:
  - a particle filter,
  - an obturator which may be selectively open or closed,
  - retention pins configured to receive a bottle previously fitted with a safety device,
  - annular edges associated to the obturator of the input door, and
  - a lid which protects the input door and covers both a spike and the retention pins,
- wherein the lid comprises a ring that links it to the input door, and the lid is jointed to the ring by a weakening line;
- wherein the output door comprises:
  - an obturator which may selectively be open or closed,
  - annular edges associated to the obturator of the output door, and
  - a lid that protects the output door and comprises a ring that links it to the output door, and the lid is jointed to the ring by a weakening line,
- wherein the input door further comprises a tube (C) provided in a lower edge of the bag,
- wherein the tube (C) is configured to receive an assembly of a tube sector of the obturator of the input door complemented by a mobile connection;
- wherein the obturator of the input door further comprises a central projection linked to the obturator of the input door by a set of radial arms, wherein the central projection is assembled in a tubular sector;
- wherein the mobile connection of the input door comprises:
  - a closure wall, which is centrally fitted with a circular opening sized in the closure wall's diameter to be fully obstructed by an end of the central projection attached to the obturator of the input door,
  - a tubular extension which configures the spike, and which flows into a chamber containing the particle filter, and
- wherein the annular edges of the ring in the lid of the input door are sized to produce a tight grasp of the ring in the lid of the input door around the mobile connection;
- wherein the annular edges of the input door are also sized to maintain an overlaying position in relation to an annular edge of an upper end of the mobile connection, creating a perimetric line which can be welded to configure a breakage region;
- wherein an annular projection is provided between the mobile connection and the obturator of the input door, and the annular projection is sized and positioned to prevent the total separation of the obturator of the input door and the mobile connection.

2. A spike-type connector for a medicament reconstitution bag, comprising:
- an input door and an output door,
- wherein the input door comprises:
  - a particle filter,
  - an obturator which may be selectively open or closed,
  - retention pins configured to receive a bottle previously fitted with a safety device,
  - annular edges associated to the obturator of the input door, and
  - a lid which protects the input door and covers both a spike and the retention pins,
- wherein the lid comprises a ring that links it to the input door, and the lid is jointed to the ring by a weakening line;
- wherein the output door comprises:
  - an obturator which may selectively be open or closed,
  - annular edges associated to the obturator of the output door, and
  - a lid that protects the output door and comprises a ring that links it to the output door, and the lid is jointed to the ring by a weakening line,
- wherein the output door further comprises a tube sector attached to a tube (C) provided in a lower edge of the bag;
- wherein the tube (C) is configured to receive an assembly of a tube sector of the obturator of the output door complemented by a mobile connection;
- wherein the obturator of the output door further comprises a central projection linked to the obturator of the output door by a set of radial arms, wherein the central projection is assembled in a tubular sector sized to fit inside the mobile connection, remaining between the tubular sector and an outlining wall of the mobile connection and an internal projection;
- wherein the mobile connection of the output door comprises:

a closure wall, which is centrally fitted with a circular opening sized in the closure wall's diameter to be fully obstructed by an end of the central projection attached to the obturator of the output door;

a tubular extension which is fitted with a luer lock attachment terminal fit;

a ring assembled around an edge of the mobile connection, wherein the ring assembled around an edge of the mobile connection forms a protection lid which covers the luer lock attachment terminal fit, and wherein the ring has annular edges sized to produce a tight grasp of the same ring around the mobile connection;

wherein the annular edges of the output door are sized to maintain a overlaying position in relation to an annular edge of an upper end of the mobile connection, creating a perimetric line which can be welded to configure a breakage region;

wherein the protection lid comprises a projection having an internal annular cut, sized to receive the luer lock attachment terminal fit;

wherein the output door further comprises annular projections provided between the mobile connection and the obturator of the output door, and the annular projections are sized and positioned to prevent the total separation of components.

3. The connector according to claim 2, wherein the mobile connection further comprises a truncated-cone shaped wall positioned between an end of the central projection of the obturator of the output door and the circular opening in the closure wall of the mobile connection;

wherein the output door may be fully or partially closed or fully or partially open, wherein markers are integrated in an external wall of the tubular sector of the obturator of the output door; and wherein annular projections are provided between the mobile connection and the obturator of the output door, and the annular projections are sized and positioned to prevent total separation of components.

* * * * *